(12) United States Patent
Bischoff et al.

(10) Patent No.: US 8,987,276 B2
(45) Date of Patent: Mar. 24, 2015

(54) SUBSTITUTED TRIAZOLYL PIPERAZINE AND TRIAZOLYL PIPERIDINE DERIVATIVES AS GAMMA SECRETASE MODULATORS

(75) Inventors: Francois Paul Bischoff, Turnhoutseweg (BE); Adriana Ingrid Velter, Turnhoutseweg (BE); Sven Franciscus Anna Van Brandt, Turnhoutseweg (BE); Didier Jean-Claude Berthelot, Turnhoutseweg (BE)

(73) Assignees: Janssen Pharmaceuticals, Inc., Titusville, NJ (US); Cellzome Limited, Brentford, Middlesex (GB)

( * ) Notice: Subject to any disclaimer, the term of this patent is extended or adjusted under 35 U.S.C. 154(b) by 0 days.

(21) Appl. No.: 14/005,598

(22) PCT Filed: Mar. 22, 2012

(86) PCT No.: PCT/EP2012/055079
§ 371 (c)(1),
(2), (4) Date: Sep. 17, 2013

(87) PCT Pub. No.: WO2012/126984
PCT Pub. Date: Sep. 27, 2012

(65) Prior Publication Data
US 2014/0011816 A1    Jan. 9, 2014

(30) Foreign Application Priority Data
Mar. 24, 2011   (EP) .................................... 11159639

(51) Int. Cl.
| A61K 31/496 | (2006.01) |
| A61K 31/506 | (2006.01) |
| C07D 249/14 | (2006.01) |
| C07D 401/04 | (2006.01) |
| C07D 401/14 | (2006.01) |
| C07D 403/04 | (2006.01) |
| C07D 249/10 | (2006.01) |

(52) U.S. Cl.
CPC ............ *C07D 403/04* (2013.01); *C07D 249/10* (2013.01); *C07D 401/14* (2013.01)
USPC ............ 514/252.19; 514/253.09; 514/254.05; 514/256; 514/318; 514/326; 544/319; 544/333; 544/295; 544/364; 544/366; 546/194; 546/210

(58) Field of Classification Search
None
See application file for complete search history.

(56) References Cited

U.S. PATENT DOCUMENTS

| 5,767,144 A | 6/1998 | Winn et al. |
| 6,114,334 A | 9/2000 | Kerrigan et al. |
| 7,923,563 B2 | 4/2011 | Kushida et al. |

| 2002/0128319 A1 | 9/2002 | Koo et al. |
| 2006/0004013 A1 | 1/2006 | Kimura et al. |
| 2008/0280948 A1 | 11/2008 | Baumann et al. |
| 2009/0062529 A1 | 3/2009 | Kimura et al. |
| 2010/0137320 A1 | 6/2010 | Huang et al. |

FOREIGN PATENT DOCUMENTS

| EP | 1757591 | 2/2007 |
| JP | 2003/502313 | 1/2003 |
| WO | WO 01/78721 | 10/2001 |
| WO | WO 01/87845 | 11/2001 |
| WO | WO 2002/069946 | 9/2002 |
| WO | WO 2004/017963 | 3/2004 |
| WO | WO 2004/076448 | 9/2004 |
| WO | WO 2004/110350 | 12/2004 |
| WO | WO 2005/016892 | 5/2005 |
| WO | WO 2005/085245 | 9/2005 |
| WO | WO 2005/115990 | 12/2005 |

(Continued)

OTHER PUBLICATIONS

Eimer et al. Molecular Neurodegeneration vol. 8, pp. 1-12 (2013).*
Citron et al. "Mutant Presenilins of Alzheimer's Disease Increase Production of 42-Residue Amyloid β-Protein in Both Transfected Cells and Transgenic Mice", Nature Medicine, Jan. 1997, 3(1), 67-72.
"Crystallization", Kirk-Othmer Encyclopedia of Chemical Technology, 2002, 8, 95-147.
Dorwald, "Side Reactions in Organic Synthesis", Wiley: VCH Weinheim Preface, Chapter 8, 45 pages, (2005).
Dyatkin et al., "Determination of the Absolute Configuration of a Key Tricyclic Component of a Novel Vasopressin Receptor Antagonist by Use of Vibrational Circular Dichroism", Chirality, 2002, 14, 215-219.

(Continued)

*Primary Examiner* — Emily Bernhardt
(74) *Attorney, Agent, or Firm* — Baker & Hostetler LLP

(57) ABSTRACT

The present invention is concerned with novel substituted triazolyl piperazine and triazolyl piperidine derivatives of Formula (I)

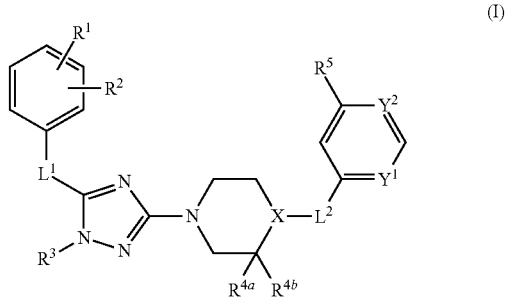

wherein $R^1$, $R^2$, $R^3$, $R^{4a}$, $R^{4b}$, $R^5$, X, $Y^1$, $Y^2$, $L^1$, and $L^2$ have the meaning defined in the claims. The compounds according to the present invention are useful as gamma secretase modulators. The invention further relates to processes for preparing such novel compounds, pharmaceutical compositions comprising said compounds as an active ingredient as well as the use of said compounds as a medicament.

12 Claims, No Drawings

(56) References Cited

FOREIGN PATENT DOCUMENTS

| WO | WO 2006/135667 | 12/2006 |
|---|---|---|
| WO | WO 2007/034252 | 3/2007 |
| WO | WO 2007/038314 | 4/2007 |
| WO | WO 2007/043786 | 4/2007 |
| WO | WO 2007/044895 | 4/2007 |
| WO | WO 2007/058942 | 5/2007 |
| WO | WO 2007/105053 | 9/2007 |
| WO | WO 2007/113276 | 10/2007 |
| WO | WO 2007/131991 | 11/2007 |
| WO | WO 2008/065199 | 6/2008 |
| WO | WO 2008/073370 | 6/2008 |
| WO | WO 2008/082490 | 7/2008 |
| WO | WO 2008/097538 | 8/2008 |
| WO | WO 2008/099210 | 8/2008 |
| WO | WO 2008/100412 | 8/2008 |
| WO | WO 2008/137139 | 11/2008 |
| WO | WO 2008/156580 | 12/2008 |
| WO | WO 2009/005729 | 1/2009 |
| WO | WO 2009/032277 | 3/2009 |
| WO | WO 2009/050227 | 4/2009 |
| WO | WO 2009/073777 | 6/2009 |
| WO | WO 2009/076352 | 6/2009 |
| WO | WO 2009/103652 | 8/2009 |
| WO | WO 2010/010188 | 1/2010 |
| WO | WO 2010/052199 | 5/2010 |
| WO | WO 2010/054067 | 5/2010 |
| WO | WO 2010/065310 | 6/2010 |
| WO | WO 2010/070008 | 6/2010 |
| WO | WO 2010/083141 | 7/2010 |
| WO | WO 2010/089292 | 8/2010 |
| WO | WO 2010/094647 | 8/2010 |
| WO | WO 2010/098487 | 9/2010 |
| WO | WO 2010/098488 | 9/2010 |
| WO | WO 2010/098495 | 9/2010 |
| WO | WO 2010/100606 | 9/2010 |
| WO | WO 2010/106745 | 9/2010 |
| WO | WO 2010/126745 | 11/2010 |
| WO | WO 2010/137320 | 12/2010 |
| WO | WO 2010/145883 | 12/2010 |
| WO | WO 2011/006903 | 1/2011 |
| WO | WO 2011/086098 | 7/2011 |
| WO | WO 2011/086099 | 7/2011 |
| WO | WO 2012/131539 | 4/2012 |
| WO | WO 2012/126984 | 9/2012 |
| WO | WO 2013/010904 | 1/2013 |

OTHER PUBLICATIONS

Eriksen et al., "NSAIDs and Enantiomers of Flurbiprofen Target Gamma-Secretase and Lower A-beta-42 In Vivo", J. Clin Invest, 2003, 112(3), 440-449.

Garofalo, "Patents Targeting Gamma-Secretase Inhibition and Modulation for the Treatment of Alzheimer's Disease: 2004-2008", Expert Opinion Ther. Patents, 2008, 18(7), 693-703.

Greene et al., "Protective Groups in Organic Synthesis", John Wiley & Sons, Inc., Third Edition, 1999, 3 pages.

Guillory (Brittain Ed.). "Polymorphism in Pharmaceutical Solids" Marcel Dekker. Inc., NY, 1999, 50 pages.

Jadhav et al. "Ammonium Metavanadate: A Novel Catalyst for Synthesis of 2-Substituted Benzimidazole Derivatives", Chinese Chemical Letters, 2009, 20, 292-295.

Jain et al., "Polymorphism in Pharmacy", Indian Drugs, 1986, 23(6), 315-329.

Larner, "Secretases as Therapeutic Targets in Alzheimer's Disease: Patents 2000-2004", Exp. Opinion Ther. Patents, 2004, 14, 1403-1420.

Marjaux et al., "γ-Secretase Inhibitors: Still in the running as Alzheimer's Therapeutics", Drug Discovery Today: Therapeutics Strategies, 2004, 1(1), 6 pages.

Matthews et al., "A Convenient Procedure for the Preparation of 4(5)-Cyanoimidazoles", J. Org. Chem., 1986 51, 3228-3231.

Moechars et al., "Early Phenotypic Changes in Transgenic Mice That Overexpress Different Mutants of Amyloid Precursor Protein in Brain", J. Biol. Chem., 1999, 274(10), 6483-6492.

Morihara et al., "Selective Inhibition of Aβ342 Production by NSAID R-Enantiomers", Journal of Neurochemistry, 2002, 83, 1009-1012.

Oumata et al., "Roscovitine-Derived, Dual-Specificity Inhibitors of Cyclin-Dependent Kinases and Casein Kinases 1", J. Med. Chem., 2008, 51, 5229-5242.

Peretto et al., "Synthesis and Biological Activity of Fluriprofen Analogues As Selective Inhibitors of β-Amyloid 1-42 Secretion", J Med Chem 2005, 48, 5705.

Schweisguth et al., "Regulation of Notch Signaling Activity", Current Biology, Feb. 3, 2004,14, R129-R138.

Sechi et al., "Design and Synthesis of Novel Indole β-Diketo Acid Derivatives as HIV-1 Integrase Inhibitors", J. Med. Chem., 2004, 47, 5298-5310.

Steiner, "Uncovering γ-Secretase", Current Alzheimer Research, 2004, 1(3), 175-181.

Tanzi et al., "Twenty Years of the Alzheimer's Disease Amyloid Hypothesis: A Genetic Perspective", Cell, 2005, 120, 545-555.

Vippagunta et al., "Crystalline Solids", Advanced Drug Delivery Reviews, 2001, 48, 3-26.

Wang et al., "Preparation of a-Chloroketones by the Chloracetate Claisen Reaction", Synlett, 2000, 6, 902-904.

Weggen et al., "A Subset of NSAIDs Lower Amyloidegenic Aβ42 Independently of Cyclooxygenase Activity", Nature, Nov. 2001, 414, 212-216.

West, "Solid State Chemistry and its Applications", Wiley, New York, 1988, 16 pages (see pp. 358 & 365).

Yu et al. "Physical Characterization of Polymorphic Drugs: An Integrated Characterization Strategy", PSTT, 1998, 1(3), 118-127.

Zettl et al., "Exploring the Chemical Space of γ-Secretase Modulators", Trends in Pharmaceutical Sciences, 2010, 31(9), 402-410.

* cited by examiner

U.S. 8,987,276 B2

SUBSTITUTED TRIAZOLYL PIPERAZINE AND TRIAZOLYL PIPERIDINE DERIVATIVES AS GAMMA SECRETASE MODULATORS

CROSS-REFERENCE TO RELATED APPLICATIONS

The present application claims priority of the benefits of the filing of Application Nos. EP 11159639.1 filed Mar. 24, 2011, and PCT/EP2012/055079 (WO2012/126984) filed Mar. 22, 2012. The complete disclosures of the aforementioned related patent applications are hereby incorporated herein by reference for all purposes.

FIELD OF THE INVENTION

The present invention is concerned with novel substituted triazolyl piperazine and triazolyl piperidine derivatives useful as gamma secretase modulators. The invention further relates to processes for preparing such novel compounds, pharmaceutical compositions comprising said compounds as an active ingredient as well as the use of said compounds as a medicament.

BACKGROUND OF THE INVENTION

Alzheimer's Disease (AD) is a progressive neurodegenerative disorder marked by loss of memory, cognition, and behavioral stability. AD afflicts 6-10% of the population over age 65 and up to 50% over age 85. It is the leading cause of dementia and the third leading cause of death after cardiovascular disease and cancer. There is currently no effective treatment for AD. The total net cost related to AD in the U.S. exceeds $100 billion annually.

AD does not have a simple etiology, however, it has been associated with certain risk factors including (1) age, (2) family history and (3) head trauma; other factors include environmental toxins and low levels of education. Specific neuropathological lesions in the limbic and cerebral cortices include intracellular neurofibrillary tangles consisting of hyperphosphorylated tau protein and the extracellular deposition of fibrillar aggregates of amyloid beta peptides (amyloid plaques). The major component of amyloid plaques are the amyloid beta (A-beta, Abeta or Aβ) peptides of various lengths. A variant thereof, which is the Aβ1-42-peptide (Abeta-42), is believed to be the major causative agent for amyloid formation. Another variant is the Aβ1-40-peptide (Abeta-40). Aβ is the proteolytic product of a precursor protein, beta amyloid precursor protein (beta-APP or APP).

Familial, early onset autosomal dominant forms of AD have been linked to missense mutations in the β-amyloid precursor protein (β-APP or APP) and in the presenilin proteins 1 and 2. In some patients, late onset forms of AD have been correlated with a specific allele of the apolipoprotein E (ApoE) gene, and, more recently, the finding of a mutation in alpha2-macroglobulin, which may be linked to at least 30% of the AD population. Despite this heterogeneity, all forms of AD exhibit similar pathological findings. Genetic analysis has provided the best clues for a logical therapeutic approach to AD. All mutations found to date, affect the quantitative or qualitative production of the amyloidogenic peptides known as Abeta-peptides (Aβ), specifically Aβ42, and have given strong support to the "amyloid cascade hypothesis" of AD (Tanzi and Bertram, 2005, Cell 120, 545). The likely link between Aβ peptide generation and AD pathology emphasizes the need for a better understanding of the mechanisms of Aβ production and strongly warrants a therapeutic approach at modulating Aβ levels.

The release of Aβ peptides is modulated by at least two proteolytic activities referred to as β- and γ-secretase cleavage at the N-terminus (Met-Asp bond) and the C-terminus (residues 37-42) of the Aβ peptide, respectively. In the secretory pathway, there is evidence that β-secretase cleaves first, leading to the secretion of s-APPβ (sβ) and the retention of a 11 kDa membrane-bound carboxy terminal fragment (CTF). The latter is believed to give rise to Aβ peptides following cleavage by γ-secretase. The amount of the longer isoform, Aβ42, is selectively increased in patients carrying certain mutations in the region of a particular gene coding in a particular protein (presenilin), and these mutations have been correlated with early-onset familial AD. Therefore, Aβ42 is believed by many researchers to be the main culprit of the pathogenesis of AD.

It has now become clear that the γ-secretase activity cannot be ascribed to a single protein, but is in fact associated with an assembly of different proteins.

The gamma (γ)-secretase activity resides within a multiprotein complex containing at least four components: the presenilin (PS) heterodimer, nicastrin, aph-1 and pen-2. The PS heterodimer consists of the amino- and carboxyterminal PS fragments generated by endoproteolysis of the precursor protein. The two aspartates of the catalytic site are at the interface of this heterodimer. It has recently been suggested that nicastrin serves as a gamma-secretase-substrate receptor. The functions of the other members of gamma-secretase are unknown, but they are all required for activity (Steiner, 2004. Curr. Alzheimer Research 1(3): 175-181).

Thus, although the molecular mechanism of the second cleavage-step has remained elusive until now, the γ-secretase-complex has become one of the prime targets in the search for compounds for the treatment of AD.

Various strategies have been proposed for targeting γ-secretase in AD, ranging from targeting the catalytic site directly, developing substrate-specific inhibitors and modulators of γ-secretase activity (Marjaux et al., 2004. Drug Discovery Today: Therapeutic Strategies, Volume 1, 1-6). Accordingly, a variety of compounds were described that have secretases as targets (Larner, 2004. Secretases as therapeutics targets in AD: patents 2000-2004. Expert Opin. Ther. Patents 14, 1403-1420).

Indeed, this finding was supported by biochemical studies in which an effect of certain Non-Steroidal Anti-Inflammatory Drugs (NSAIDs) on γ-secretase was shown (US 2002/0128319; Eriksen (2003) J. Clin. Invest. 112, 440). Potential limitations for the use of NSAIDs to prevent or treat AD are their inhibition activity of cyclooxygenase (COX) enzymes, which can lead to unwanted side effects, and their low CNS penetration (Peretto et al., 2005, J. Med. Chem. 48, 5705-5720). More recently the NSAID R-flurbiprofen, an enantiomer lacking Cox-inhibitory activity and related gastric toxicity, has failed in large phase III trial since the drug did not improve thinking ability or the ability of patients to carry out daily activities significantly more than those patients on placebo.

WO-2009/103652 relates to 1H-1,2,4-triazol-3-amine derivatives as modulators for Aβ;

WO-2009/032277 relates to heterocyclic compounds useful as γ secretase modulators;

WO-2010/010188 relates to [1,2,4]triazolo-[1,5-a]pyridine compounds, useful for the treatment of degenerative joint diseases and inflammatory diseases;

WO-2010/098495 relates to imidazolylpyrazine derivatives as therapeutic agents for AD;
WO-2008/099210 relates to piperazine derivatives for treatment of AD and related conditions; and
WO-2008/100412 provides compounds useful for treating diseases associated with the deposition of β-amyloid peptide in the brain.

There is a strong need for novel compounds which modulate γ-secretase activity thereby opening new avenues for the treatment of AD. It is an object of the present invention to overcome or ameliorate at least one of the disadvantages of the prior art, or to provide a useful alternative. The compounds of the present invention or part of the compounds of the present invention may have improved metabolic stability properties, improved central brain availability, improved solubilities, or reduced CYP inhibition compared with the compounds disclosed in the prior art. It is accordingly an object of the present invention to provide such novel compounds.

SUMMARY OF THE INVENTION

It has been found that the compounds of the present invention are useful as γ secretase modulators. The compounds according to the invention and the pharmaceutically acceptable compositions thereof, may be useful in the treatment or prevention of AD.

The present invention concerns novel compounds of Formula (I)

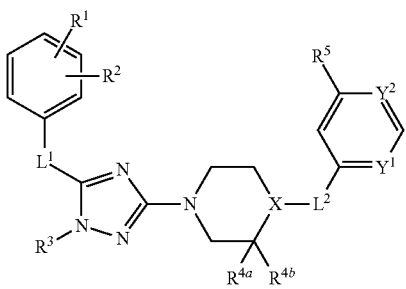

(I)

and stereoisomeric forms thereof, wherein
$R^1$ and $R^2$ independently are selected from the group consisting of hydrogen, halo, $C_{1-4}$alkyl, $C_{1-4}$alkyloxy, $C_{1-4}$alkyl substituted with one or more halo substituents, and $C_{1-4}$alkyloxy substituted with one or more halo substituents;
$L^1$ is $NR^6$, O, carbonyl or a covalent bond; wherein $R^6$ is hydrogen or $C_{1-4}$alkyl;
$R^3$ represents $C_{1-4}$alkyl;
$R^{4a}$ and $R^{4b}$ independently are selected from the group consisting of hydrogen and $C_{1-4}$alkyl;
X is N or CH;
$L^2$ is O, $CH_2$ or a covalent bond; provided that when $L^2$ is O, then X is CH;
$R^5$ is hydrogen or $C_{1-4}$alkyl;
$Y^1$ is CH or N;
$Y^2$ is $CR^7$ or N; wherein $R^7$ represents H or $C_{1-4}$alkyloxy;
and the pharmaceutically acceptable addition salts, and the solvates thereof.

The present invention also concerns methods for the preparation of compounds of Formula (I) and pharmaceutical compositions comprising them.

The present compounds were found to modulate the γ-secretase activity in vitro and in vivo, and therefore may be useful in the treatment or prevention of AD, traumatic brain injury (TBI), mild cognitive impairment (MCI), senility, dementia, dementia with Lewy bodies, cerebral amyloid angiopathy, multi-infarct dementia, Down's syndrome, dementia associated with Parkinson's disease and dementia associated with beta-amyloid, preferably AD and other disorders with Beta-amyloid pathology (e.g. glaucoma).

In view of the aforementioned pharmacology of the compounds of Formula (I), it follows that they may be suitable for use as a medicament.

More especially the compounds may be suitable in the treatment or prevention of AD, cerebral amyloid angiopathy, multi-infarct dementia, dementia pugilistica or Down syndrome.

The present invention also concerns to the use of a compound according to the general Formula (I), the stereoisomeric forms thereof and the pharmaceutically acceptable acid or base addition salts and the solvates thereof, for the manufacture of a medicament for the modulation of γ-secretase activity.

Use of a compound of Formula (I) for the modulation of γ-secretase activity resulting in a decrease in the relative amount of Aβ42-peptides produced is preferred. One advantage of the compounds or a part of the compounds of the present invention may lie in their enhanced CNS-penetration.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION

When describing the compounds of the invention, the terms used are to be construed in accordance with the following definitions, unless a context dictates otherwise.

Whenever the term "substituted" is used in the present invention, it is meant, unless otherwise is indicated or is clear from the context, to indicate that one or more hydrogens, in particular from 1 to 4 hydrogens, preferably from 1 to 3 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

The term "halo" as a group or part of a group is generic for fluoro, chloro, bromo, iodo unless otherwise is indicated or is clear from the context.

The term "$C_{1-4}$alkyl" as a group or part of a group refers to a hydrocarbyl radical of Formula $C_nH_{2n+1}$ wherein n is a number ranging from 1 to 4. $C_{1-4}$alkyl groups comprise from 1 to 4 carbon atoms, preferably from 1 to 3 carbon atoms, more preferably 1 to 2 carbon atoms. $C_{1-4}$alkyl groups may be linear or branched and may be substituted as indicated herein. When a subscript is used herein following a carbon atom, the subscript refers to the number of carbon atoms that the named group may contain. $C_{1-4}$alkyl includes all linear, or branched alkyl groups with between 1 and 4 carbon atoms, and thus includes such as for example methyl, ethyl, n-propyl, i-propyl, 2-methyl-ethyl, butyl and its isomers (e.g. n-butyl, isobutyl and tert-butyl), and the like.

The term "$C_{1-4}$alkyloxy" as a group or part of a group refers to a radical having the Formula $OR^b$ wherein $R^b$ is $C_{1-4}$alkyl. Non-limiting examples of suitable $C_{1-4}$alkyloxy include methyloxy (also methoxy), ethyloxy (also ethoxy), propyloxy, isopropyloxy, butyloxy, isobutyloxy, sec-butyloxy and tert-butyloxy.

The chemical names of the compounds of the present invention were generated according to the nomenclature rules agreed upon by the Chemical Abstracts Service, using Advanced Chemical Development, Inc., nomenclature software (ACD/Labs Release 12.00 Product version 12.01; Build 33104, 27 May 2009).

In case of tautomeric forms, it should be clear that the other non-depicted tautomeric form is also included within the scope of the present invention.

The following numbering was used to indicate the point of attachment of $R^1$ and $R^2$ to the remainder of the molecule:

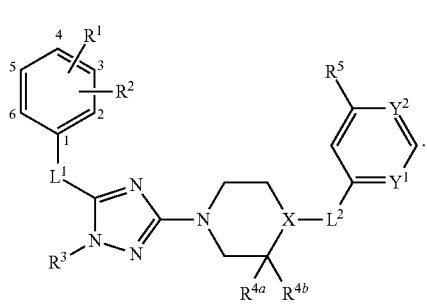

(I)

When any variable occurs more than one time in any constituent, each definition is independent.

It will be appreciated that some of the compounds of Formula (I) and their pharmaceutically acceptable addition salts and solvates may contain one or more centers of chirality and exist as stereoisomeric forms.

As used in the description, whenever the term "compound(s) of formula (I)" is used, it is meant to include the addition salts, the solvates and the stereoisomers thereof.

The terms "stereoisomers", "stereoisomeric forms" or "stereochemically isomeric forms" hereinbefore or hereinafter are used interchangeably.

The term "stereoisomeric forms" as used hereinbefore defines all the possible isomeric forms that the compounds of Formula (I) may possess. Unless otherwise mentioned or indicated, the chemical designation of compounds denotes the mixture of all possible stereochemically isomeric forms.

The invention includes all stereoisomers of the compound of Formula (I) either as a pure stereoisomer or as a mixture of two or more stereoisomers. The definition of "compound of formula (I)" inherently includes all stereoisomers of the compound of formula (I) either as a pure stereoisomer or as a mixture of two or more stereoisomers. Enantiomers are stereoisomers that are non-superimposable mirror images of each other. A 1:1 mixture of a pair of enantiomers is a racemate or racemic mixture. Diastereomers (or diastereoisomers) are stereoisomers that are not enantiomers, i.e. they are not related as mirror images. More in particular, stereogenic centers may have the R- or S-configuration; substituents on bivalent cyclic (partially) saturated radicals may have either the cis- or trans-configuration. If a compound contains a double bond, the substituents may be in the E or the Z configuration at said double bond. Stereoisomeric forms of the compounds of Formula (I) are embraced within the scope of this invention. Therefore, the invention includes enantiomers, diastereomers, racemates, E isomers, Z isomers, cis isomers, trans isomers and mixtures thereof, whenever chemically possible.

The absolute configuration is specified according to the Cahn-Ingold-Prelog system. The configuration at an asymmetric atom is specified by either R or S. Resolved compounds whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other isomers. Thus, when a compound of formula (I) is for instance specified as (R), this means that the compound is substantially free of the (S) isomer; when a compound of formula (I) is for instance specified as E, this means that the compound is substantially free of the Z isomer; when a compound of formula (I) is for instance specified as cis, this means that the compound is substantially free of the trans isomer.

For therapeutic use, salts of the compounds of Formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove or hereinafter are meant to comprise the therapeutically active non-toxic acid and base addition salt forms which the compounds of Formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the hydrates and solvent addition forms which the compounds of Formula (I) are able to form, as well as the salts thereof. Examples of such forms are e.g. hydrates, alcoholates and the like.

The compounds of Formula (I) as prepared in the processes described below may be synthesized in the form of racemic mixtures of enantiomers that can be separated from one another following art-known resolution procedures. An manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

In the framework of this application, a compound according to the invention is inherently intended to comprise all isotopic combinations of its chemical elements. In the framework of this application, a chemical element, in particular when mentioned in relation to a compound according to Formula (I), comprises all isotopes and isotopic mixtures of this element. For example, when hydrogen is mentioned, it is understood to refer to $^1H$, $^2H$, $^3H$ and mixtures thereof.

A compound according to the invention therefore inherently comprises a compound with one or more isotopes of one or more element, and mixtures thereof, including a radioactive compound, also called radiolabelled compound, wherein one or more non-radioactive atoms has been replaced by one of its radioactive isotopes. By the term "radiolabelled compound" is meant any compound according to Formula (I), or a pharmaceutically acceptable salt thereof, which contains at least one radioactive atom. For example, a compound can be labelled with positron or with gamma emitting radioactive isotopes. For radioligand-binding techniques, the $^3H$-atom or the $^{125}I$-atom is the atom of choice to be replaced. For imaging, the most commonly used positron emitting (PET) radioactive isotopes are $^{11}C$, $^{18}F$, $^{15}O$ and $^{13}N$, all of which are accelerator produced and have half-lives of 20, 100, 2 and 10 minutes (min) respectively. Since the half-lives of these radioactive isotopes are so short, it is only feasible to use them at institutions which have an accelerator on site for their production, thus limiting their use. The most widely used of these are $^{18}F$, $^{99m}Tc$, $^{201}Tl$ and $^{123}I$. The handling of these radioactive isotopes, their production, isolation and incorporation in a molecule are known to the skilled person.

In particular, the radioactive atom is selected from the group of hydrogen, carbon, nitrogen, sulfur, oxygen and halogen. In particular, the radioactive isotope is selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$.

As used in the specification and the appended claims, the singular forms "a", "an," and "the" also include plural referents unless the context clearly dictates otherwise. For example, "a compound" means 1 compound or more than 1 compound.

The terms described above and others used in the specification are well understood to those in the art.

Preferred features of the compounds of this invention are now set forth.

In an embodiment, the present invention concerns novel compounds of Formula (I):

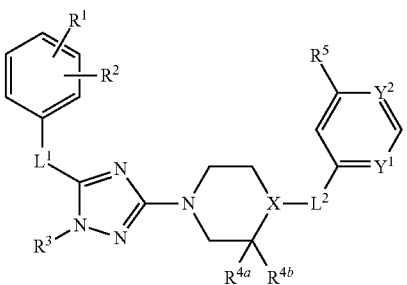

and stereoisomeric forms thereof, wherein $R^1$ and $R^2$ independently are selected from the group consisting of hydrogen, halo, $C_{1-4}$alkyl, $C_{1-4}$alkyloxy, $C_{1-4}$alkyl substituted with one or more halo substituents, and $C_{1-4}$alkyloxy substituted with one or more halo substituents;

$L^1$ is $NR^6$, O, carbonyl or a covalent bond; wherein $R^6$ is hydrogen or $C_{1-4}$alkyl;

$R^3$ represents $C_{1-4}$alkyl;

$R^{4a}$ and $R^{4b}$ independently are selected from the group consisting of hydrogen and $C_{1-4}$alkyl;

X is N or CH;

$L^2$ is O, $CH_2$ or a covalent bond; provided that when $L^2$ is O, then X is CH;

$R^5$ is hydrogen or $C_{1-4}$alkyl;

$Y^1$ is CH or N;

$Y^2$ is $CR^7$ or N; wherein $R^7$ represents H or $C_{1-4}$alkyloxy;

and the pharmaceutically acceptable addition salts, and the solvates thereof.

In an embodiment, the present invention concerns novel compounds of Formula (I) and stereoisomeric forms thereof, wherein $R^1$ and $R^2$ independently are selected from the group consisting of hydrogen, halo, $C_{1-4}$alkyl, $C_{1-4}$alkyloxy, $C_{1-4}$alkyl substituted with one or more halo substituents, and $C_{1-4}$alkyloxy substituted with one or more halo substituents;

$L^1$ is $NR^6$, O, carbonyl or a covalent bond; wherein $R^6$ is hydrogen or $C_{1-4}$alkyl; $R^3$ represents $C_{1-4}$alkyl;

$R^{4a}$ and $R^{4b}$ are the same and both represent hydrogen or $C_{1-4}$alkyl;

X is N or CH;

$L^2$ is O, $CH_2$ or a covalent bond; provided that when $L^2$ is O, then X is CH;

$R^5$ is hydrogen or $C_{1-4}$alkyl;

$Y^1$ is CH or N;

$Y^2$ is $CR^7$ or N; wherein $R^7$ represents H or $C_{1-4}$alkyloxy;

and the pharmaceutically acceptable addition salts, and the solvates thereof.

In an embodiment, the present invention concerns novel compounds of Formula (I) and stereoisomeric forms thereof, wherein $R^1$ is selected from the group consisting of halo, $C_{1-4}$alkyl, $C_{1-4}$alkyloxy, $C_{1-4}$alkyl substituted with one or more halo substituents, and $C_{1-4}$alkyloxy substituted with one or more halo substituents;

$R^2$ is selected from the group consisting of hydrogen, halo, $C_{1-4}$alkyl, $C_{1-4}$alkyloxy, $C_{1-4}$alkyl substituted with one or more halo substituents, and $C_{1-4}$alkyloxy substituted with one or more halo substituents;

$L^1$ is $NR^6$, O, carbonyl or a covalent bond; wherein $R^6$ is hydrogen or $C_{1-4}$alkyl;

$R^3$ represents $C_{1-4}$alkyl;

$R^{4a}$ and $R^{4b}$ are the same and both represent hydrogen or $C_{1-4}$alkyl;
X is N or CH;
$L^2$ is O, $CH_2$ or a covalent bond; provided that when $L^2$ is O, then X is CH;
$R^5$ is hydrogen or $C_{1-4}$alkyl;
$Y^1$ is CH or N;
$Y^2$ is $CR^7$ or N; wherein $R^7$ represents H or $C_{1-4}$alkyloxy;
and the pharmaceutically acceptable addition salts, and the solvates thereof.

In an embodiment, the present invention concerns novel compounds of Formula (I) and stereoisomeric forms thereof, wherein
$R^1$ and $R^2$ independently are selected from the group consisting of halo, $C_{1-4}$alkyl, $C_{1-4}$alkyloxy, $C_{1-4}$alkyl substituted with one or more halo substituents, and $C_{1-4}$alkyloxy substituted with one or more halo substituents;
$L^1$ is $NR^6$, O, carbonyl or a covalent bond; wherein $R^6$ is hydrogen or $C_{1-4}$alkyl;
$R^3$ represents $C_{1-4}$alkyl;
$R^{4a}$ and $R^{4b}$ are the same and both represent hydrogen or $C_{1-4}$alkyl;
X is N or CH;
$L^2$ is O, $CH_2$ or a covalent bond; provided that when $L^2$ is O, then X is CH;
$R^5$ is hydrogen or $C_{1-4}$alkyl;
$Y^1$ is CH or N;
$Y^2$ is $CR^7$ or N; wherein $R^7$ represents H or $C_{1-4}$alkyloxy;
and the pharmaceutically acceptable addition salts, and the solvates thereof.

In an embodiment, the present invention concerns novel compounds of Formula (I) and stereoisomeric forms thereof, wherein
$R^1$ and $R^2$ independently are selected from the group consisting of hydrogen, halo, $C_{1-4}$alkyl, $C_{1-4}$alkyl substituted with one or more halo substituents, and $C_{1-4}$alkyloxy substituted with one or more halo substituents;
$L^1$ is NH or a covalent bond;
$R^3$ represents $C_{1-4}$alkyl;
$R^{4a}$ and $R^{4b}$ are the same and both represent hydrogen or $C_{1-4}$alkyl;
X is N or CH;
$L^2$ is O, $CH_2$ or a covalent bond; provided that when $L^2$ is O, then X is CH;
$R^5$ is hydrogen or $C_{1-4}$alkyl;
$Y^1$ is CH or N;
$Y^2$ is $CR^7$ or N; wherein $R^7$ represents $C_{1-4}$alkyloxy;
and the pharmaceutically acceptable addition salts, and the solvates thereof.

In an embodiment, the present invention concerns novel compounds of Formula (I) and stereoisomeric forms thereof, wherein
$R^1$ and $R^2$ independently are selected from the group consisting of hydrogen, halo, methyl, methyl substituted with one or more halo substituents, and methoxy substituted with one or more halo substituents;
$L^1$ is NH or a covalent bond;
$R^3$ represents methyl;
$R^{4a}$ and $R^{4b}$ are the same and both represent hydrogen or methyl;
X is N or CH;
$L^2$ is O, $CH_2$ or a covalent bond; provided that when $L^2$ is O, then X is CH;
$R^5$ is hydrogen or methyl;
$Y^1$ is CH or N;
$Y^2$ is $CR^7$ or N; wherein $R^7$ represents methoxy;
and the pharmaceutically acceptable addition salts, and the solvates thereof.

In an embodiment, the present invention concerns novel compounds of Formula (I) and stereoisomeric forms thereof, wherein
$R^1$ and $R^2$ independently are selected from the group consisting of hydrogen, fluoro, methyl, trifluoromethyl, and trifluoromethoxy;
$L^1$ is NH or a covalent bond;
$R^3$ represents methyl;
$R^{4a}$ and $R^{4b}$ are the same and both represent hydrogen or methyl;
X is N or CH;
$L^2$ is O, $CH_2$ or a covalent bond; provided that when $L^2$ is O, then X is CH;
$R^5$ is hydrogen or methyl;
$Y^1$ is CH or N;
$Y^2$ is $CR^7$ or N; wherein $R^7$ represents methoxy;
and the pharmaceutically acceptable addition salts, and the solvates thereof.

In an embodiment, the present invention concerns novel compounds of Formula (I) and stereoisomeric forms thereof, wherein
$R^1$ is selected from the group consisting of fluoro, methyl, trifluoromethyl and trifluoromethyloxy;
$R^2$ is selected from the group consisting of hydrogen, fluoro, methyl, and trifluoromethyl;
$L^1$ is NH or a covalent bond;
$R^3$ represents methyl;
$R^{4a}$ and $R^{4b}$ are the same and both represent hydrogen or methyl;
X is N or CH;
$L^2$ is O, $CH_2$ or a covalent bond; provided that when $L^2$ is O, then X is CH;
$R^5$ is hydrogen or methyl;
$Y^1$ is CH or N;
$Y^2$ is $CR^7$ or N; wherein $R^7$ represents methoxy;
and the pharmaceutically acceptable addition salts, and the solvates thereof.

An embodiment of the present invention relates to those compounds of Formula (I) and stereoisomeric forms thereof, or any subgroup thereof as mentioned in any of the other embodiments, wherein $R^1$ is in the 2-position, and $R^2$ is in the 5-position.

An embodiment of the present invention relates to those compounds of Formula (I) and stereoisomeric forms thereof, or any subgroup thereof as mentioned in any of the other embodiments, wherein $R^1$ represents fluoro and is in the 2-position, and $R^2$ represents trifluoromethyl and is in the 5-position.

An embodiment of the present invention relates to those compounds of Formula (I) and stereoisomeric forms thereof, or any subgroup thereof as mentioned in any of the other embodiments, wherein $R^1$ is in the 2-position, and $R^2$ is in the 4-position.

An embodiment of the present invention relates to those compounds of Formula (I) and stereoisomeric forms thereof, or any subgroup thereof as mentioned in any of the other embodiments, wherein $R^1$ represents methyl and is in the 2-position, and $R^2$ represents hydrogen or fluoro and is in the 4-position.

An embodiment of the present invention relates to those compounds of Formula (I) and stereoisomeric forms thereof, or any subgroup thereof as mentioned in any of the other embodiments, wherein $R^1$ is in the 2-position and is selected from the group consisting of halo, $C_{1-4}$alkyl, $C_{1-4}$alkyloxy, $C_{1-4}$alkyl substituted with one or more halo substituents, and $C_{1-4}$alkyloxy substituted with one or more halo substituents; and wherein $R^2$ is selected from the group consisting of hydrogen, halo, $C_{1-4}$alkyl, $C_{1-4}$alkyloxy, $C_{1-4}$alkyl substituted with one or more halo substituents, and $C_{1-4}$alkyloxy substituted with one or more halo substituents.

An embodiment of the present invention relates to those compounds of Formula (I) and stereoisomeric forms thereof, or any subgroup thereof as mentioned in any of the other embodiments, wherein $R^1$ is in the 2-position and wherein $R^2$ is in any of the other positions; and wherein $R^1$ and $R^2$ independently are selected from the group consisting of halo, $C_{1-4}$alkyl, $C_{1-4}$alkyloxy, $C_{1-4}$alkyl substituted with one or more halo substituents, and $C_{1-4}$alkyloxy substituted with one or more halo substituents.

An embodiment of the present invention relates to those compounds of Formula (I) and stereoisomeric forms thereof, or any subgroup thereof as mentioned in any of the other embodiments, wherein $R^1$ is in the 2-position and is selected from the group consisting of fluoro, methyl or trifluoromethyl.

An embodiment of the present invention relates to those compounds of Formula (I) and stereoisomeric forms thereof, or any subgroup thereof as mentioned in any of the other embodiments, wherein at least one of $R^1$ and $R^2$ is other than hydrogen.

An embodiment of the present invention relates to those compounds of Formula (I) and stereoisomeric forms thereof, or any subgroup thereof as mentioned in any of the other embodiments, wherein $R^1$ is in the 2-position.

Another embodiment of the present invention relates to those compounds of Formula (I) and stereoisomeric forms thereof, or any subgroup thereof as mentioned in any of the other embodiments, wherein one or more of the following restrictions apply:
(a) $R^1$ represents methyl and is in the 2-position, and $R^2$ represents hydrogen or fluoro and is in the 4-position;
(b) $L^1$ is NH;
(c) $R^3$ represents methyl;
(d) $R^{4a}$ and $R^{4b}$ are the same and both represent methyl;
(e) X is N, and $L^2$ is $CH_2$ or a covalent bond; in particular X is N and $L^2$ is a covalent bond;
(f) $R^5$ is hydrogen;
(g) $Y^1$ is CH;
(h) $Y^2$ is $CR^7$; wherein $R^7$ represents methoxy.

An embodiment of the present invention relates to those compounds of Formula (I) and stereoisomeric forms thereof, or any subgroup thereof as mentioned in any of the other embodiments, wherein $L^1$ is $NR^6$ or a covalent bond; in particular $NR^6$; more in particular NH.

An embodiment of the present invention relates to those compounds of Formula (I) and stereoisomeric forms thereof, or any subgroup thereof as mentioned in any of the other embodiments, wherein $R^{4a}$ and $R^{4b}$ are the same and both represent methyl.

An embodiment of the present invention relates to those compounds of Formula (I) and stereoisomeric forms thereof, or any subgroup thereof as mentioned in any of the other embodiments, wherein X is N, and $L^2$ is $CH_2$ or a covalent bond; in particular X is N and $L^2$ is a covalent bond.

An embodiment of the present invention relates to those compounds of Formula (I) and stereoisomeric forms thereof, or any subgroup thereof as mentioned in any of the other embodiments, wherein X is CH.

An embodiment of the present invention relates to those compounds of Formula (I) and stereoisomeric forms thereof, or any subgroup thereof as mentioned in any of the other embodiments, wherein $L^2$ is a covalent bond.

An embodiment of the present invention relates to those compounds of Formula (I) and stereoisomeric forms thereof, or any subgroup thereof as mentioned in any of the other embodiments, wherein $L^2$ is a O or $CH_2$; provided that when $L^2$ is O, then X is CH; in particular $L^2$ is $CH_2$.

An embodiment of the present invention relates to those compounds of Formula (I) and stereoisomeric forms thereof, or any subgroup thereof as mentioned in any of the other embodiments, wherein $Y^1$ is CH; and $Y^2$ is $CR^7$; wherein $R^7$ represents methoxy.

An embodiment of the present invention relates to those compounds of Formula (I) and stereoisomeric forms thereof, or any subgroup thereof as mentioned in any of the other embodiments, wherein at least one of $Y^1$ and $Y^2$ represents N.

An embodiment of the present invention relates to those compounds of Formula (I) and stereoisomeric forms thereof, or any subgroup thereof as mentioned in any of the other embodiments, wherein $R^7$ represents methoxy.

In an embodiment the compound of Formula (I) is selected from the group consisting of:

1-[5-(4-fluorophenyl)-1-methyl-1H-1,2,4-triazol-3-yl]-4-(4-methoxyphenyl)-piperazine, N-[2-fluoro-5-(trifluoromethyl)phenyl]-1-methyl-3-[4-[(2-methyl-4-pyridinyl)oxy]-1-piperidinyl]-1H-1,2,4-triazol-5-amine, N-[2-fluoro-5-(trifluoromethyl)phenyl]-3-[4-(4-methoxyphenyl)-3,3-dimethyl-1-piperazinyl]-1-methyl-1H-1,2,4-triazol-5-amine, N-[2-fluoro-5-(trifluoromethyl)phenyl]-1-methyl-3-[4-(4-pyridinylmethyl)-1-piperazinyl]-1H-1,2,4-triazol-5-amine, N-[2-fluoro-5-(trifluoromethyl)phenyl]-1-methyl-3-[4-[(2-methyl-4-pyridinyl)methyl]-1-piperidinyl]-1H-1,2,4-triazol-5-amine, N-[2-fluoro-5-(trifluoromethyl)phenyl]-1-methyl-3-[4-[(2-methyl-4-pyridinyl)methyl]-1-piperidinyl]-1H-1,2,4-triazol-5-amine.$HCl.H_2O$, N-[2-fluoro-5-(trifluoromethyl)phenyl]-1-methyl-3-[4-(4-pyridinyl)-1-piperazinyl]-1H-1,2,4-triazol-5-amine, N-[2-fluoro-5-(trifluoromethyl)phenyl]-3-[4-(4-methoxyphenyl)-1-piperazinyl]-1-methyl-1H-1,2,4-triazol-5-amine, N-[2-fluoro-5-(trifluoromethyl)phenyl]-1-methyl-3-[4-[(6-methyl-4-pyrimidinyl)oxy]-1-piperidinyl]-1H-1,2,4-triazol-5-amine, N-[2-fluoro-5-(trifluoromethyl)phenyl]-1-methyl-3-[4-(4-pyridinyloxy)-1-piperidinyl]-1H-1,2,4-triazol-5-amine, N-(4-fluoro-2-methylphenyl)-3-[4-(4-methoxyphenyl)-3,3-dimethyl-1-piperazinyl]-1-methyl-1H-1,2,4-triazol-5-amine, N-(4-fluoro-2-methylphenyl)-3-[4-(4-methoxyphenyl)-3,3-dimethyl-1-piperazinyl]-1-methyl-1H-1,2,4-triazol-5-amine.1.2HCl. 1.5$H_2O$, N-[3-fluoro-5-(trifluoromethyl)phenyl]-3-[4-(4-methoxyphenyl)-3,3-dimethyl-1-piperazinyl]-1-methyl-1H-1,2,4-triazol-5-amine, N-[3-fluoro-5-(trifluoromethyl)phenyl]-3-[4-(4-methoxyphenyl)-3,3-dimethyl-1-piperazinyl]-1-methyl-1H-1,2,4-triazol-5-amine.0.8HCl, 3-[4-(4-methoxyphenyl)-3,3-dimethyl-1-piperazinyl]-1-methyl-N-(2-methylphenyl)-1H-1,2,4-triazol-5-amine, 3-[4-(4-methoxyphenyl)-3,3-dimethyl-1-piperazinyl]-1-methyl-N-[3-(trifluoromethoxy)phenyl]-1H-1,2,4-triazol-5-amine, 3-[4-(4-methoxyphenyl)-3,3-dimethyl-1-piperazinyl]-1-methyl-N-[3-(trifluoromethoxy)phenyl]-1H-1,2,4-triazol-5-amine.HCl, N-[3-fluoro-2-(trifluoromethyl)phenyl]-3-[4-(4-methoxyphenyl)-3,3-dimethyl-1-piperazinyl]-1-methyl-1H-1,2,4-triazol-5-amine, 3-[4-(4-methoxyphenyl)-3,3-dimethyl-1-piperazinyl]-1-methyl-N-[2-(trifluoromethyl)phenyl]-1H-1,2,4-triazol-5-amine, and 3-[4-(5-methoxy-2-pyridinyl)-1-piperazinyl]-1-methyl-N-(2-methylphenyl)-1H-1,2,4-triazol-5-amine, stereoisomeric forms thereof, and the pharmaceutically acceptable addition salts and the solvates thereof.

In an embodiment the compound of Formula (I) is selected from the group consisting of:

3-[4-(4-methoxyphenyl)-3,3-dimethyl-1-piperazinyl]-1-methyl-N-(2-methylphenyl)-1H-1,2,4-triazol-5-amine, N-(4-fluoro-2-methylphenyl)-3-[4-(4-methoxyphenyl)-3,3-dimethyl-1-piperazinyl]-1-methyl-1H-1,2,4-triazol-5-amine, and N-(4-fluoro-2-methylphenyl)-3-[4-(4-methoxyphenyl)-3,3-dimethyl-1-piperazinyl]-1-methyl-1H-1,2,4-triazol-5-amine.1.2HCl.1.5 $H_2O$, stereoisomeric forms thereof, and the pharmaceutically acceptable addition salts and the solvates thereof.

In an embodiment the compound of Formula (I) is 3-[4-(4-methoxyphenyl)-3,3-dimethyl-1-piperazinyl]-1-methyl-N-(2-methylphenyl)-1H-1,2,4-triazol-5-amine or N-(4-fluoro-2-methylphenyl)-3-[4-(4-methoxyphenyl)-3,3-dimethyl-1-piperazinyl]-1-methyl-1H-1,2,4-triazol-5-amine.1.2HCl.1.5 $H_2O$.

All possible combinations of the above-indicated interesting embodiments are considered to be embraced within the scope of this invention.

Preparation of the Compounds

The present invention also encompasses processes for the preparation of compounds of Formula (I) and subgroups thereof. In the reactions described, it can be necessary to protect reactive functional groups, for example hydroxy, amino, or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1999.

The compounds of Formula (I) and the subgroups thereof can be prepared by a succession of steps as described hereunder. They are generally prepared from starting materials which are either commercially available or prepared by standard means obvious to those skilled in the art. The compounds of the present invention can be also prepared using standard synthetic processes commonly used by those skilled in the art of organic chemistry.

The general preparation of some typical examples is shown below:

Experimental Procedure 1

Scheme 1

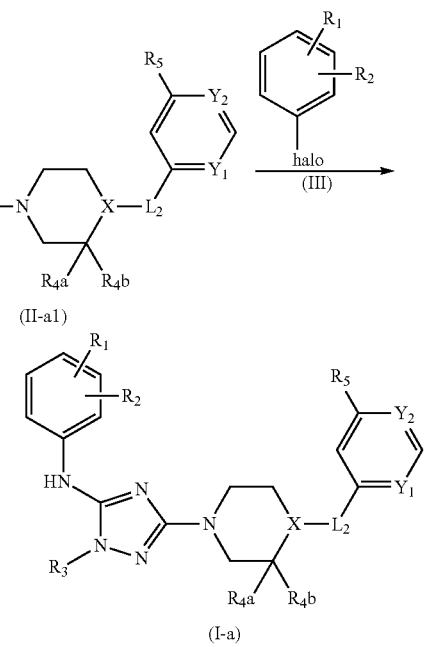

A compound of formula (I) wherein $L^1$ is $NR^6$ and $R^6$ is hydrogen, hereby named (I-a) can be prepared via a coupling reaction between an intermediate of formula (II-a1) with an appropriate aryl halide of Formula (III). In Scheme 1, halo is defined as Cl, Br or I and all variables are defined as hereinbefore. This reaction may be performed in the presence of a suitable base such as, for example, $Cs_2CO_3$ or sodium tert-butoxide. The reaction can be performed in a reaction-inert solvent such as, for example, toluene, N,N-dimethylformamide (DMF), 1,2-dimethoxyethane (DME), tert-butanol or dioxane. The reaction typically is performed in the presence of a catalyst system comprising of a suitable catalyst such as tris(dibenzylideneacetone)dipalladium ($Pd_2(dba)_3$), palladium(II) acetate ($Pd(OAc)_2$) and a ligand such as (9,9-dimethyl-9H-xanthene-4,5-diyl)bis[diphenylphosphine](Xantphos), [1,1'-binaphthalene]-2,2'-diylbis[diphenylphosphine] (BINAP), bis(2-diphenylphosphinophenyl)ether (DPEphos), or dicyclohexyl[2',4',6'-tris(1-methylethyl) [1,1'-biphenyl]-2-yl]-phosphine (X-phos). Preferably this reaction is carried out under an inert atmosphere, such as a nitrogen or an argon atmosphere. Reaction rate and yield may be enhanced by microwave assisted heating.

Palladium traces present after work-up of the reaction can optionally be removed by treatment of a solution of the compound of formula (I) in a suitable solvent or in a mixture of solvents, such as, for example DCM and MeOH, with N-acetyl-L-cysteine or thiol-functionalized silica.

Alternatively, a compound of formula (I-a) can also be prepared by a copper catalysed reaction of an intermediate of formula (II-a1) with an appropriate aryl halide of Formula (III) wherein all variables are defined as mentioned hereabove. The reaction may be performed under a protecting atmosphere such as, for example, $N_2$ atmosphere. Stirring, elevated temperatures (for example between 70-200° C.) and/or pressure may enhance the rate of the reaction. The reaction typically is performed in an organic solvent such as, for example, dimethylsulfoxide (DMSO) or dimethylformamide (DMF). Optionally, the reaction is performed in the presence of a base such as, for example $K_2CO_3$, $Cs_2CO_3$, or triethylamine ($Et_3N$), and/or a ligand such as N,N'-dimethylethylenediamine or 1,10-phenanthroline. A copper catalyst such as copper salts, for example, copper(I)oxide, copper(I)iodide, or copper(I)bromide, can be used in catalytic or stoichiometric amounts.

Experimental Procedure 2

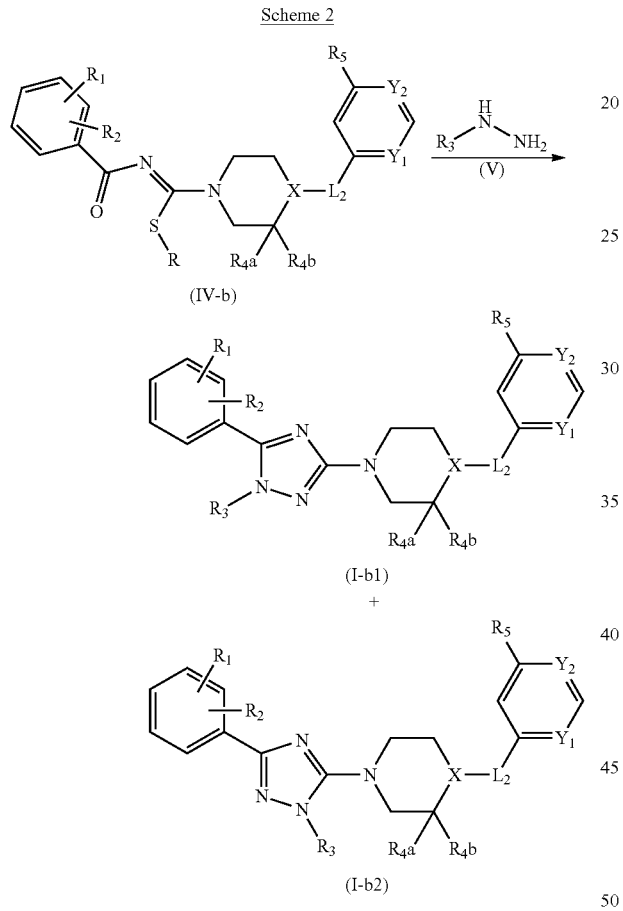

A compound of formula (I) wherein $L_1$ is a covalent bond, hereby named (I-b1) can be prepared via a condensation reaction between an intermediate of formula (IV-b) wherein R represents an alkyl substituent with an appropriate hydrazine derivative of Formula (V) according to Scheme 2. The reaction can be performed in a reaction-inert solvent such as, for example, toluene, N,N-dimethylformamide (DMF), 1,2-dimethoxyethane (DME), tert-butanol or dioxane. Stirring and elevated temperatures (for example between 70-120° C.) may enhance the rate of the reaction. R could be selected from the group consisting of for example methyl and ethyl.

During this reaction, also the regio-isomer of formula (I-b2) is usually formed.

Experimental Procedure 3

An intermediate of formula (II-a1) can be prepared via a condensation reaction between an intermediate of formula (VI-a) with an appropriate hydrazine derivative of Formula (V) according to Scheme 3. The reaction can be performed in a reaction-inert solvent such as, for example, toluene, N,N-dimethylformamide (DMF), 1,2-dimethoxyethane (DME), tert-butanol, iso-propanol or dioxane. Stirring and elevated temperatures (for example between 70-120° C.) may enhance the rate of the reaction.

During this reaction, also the regio-isomer of formula (II-a2) is usually formed.

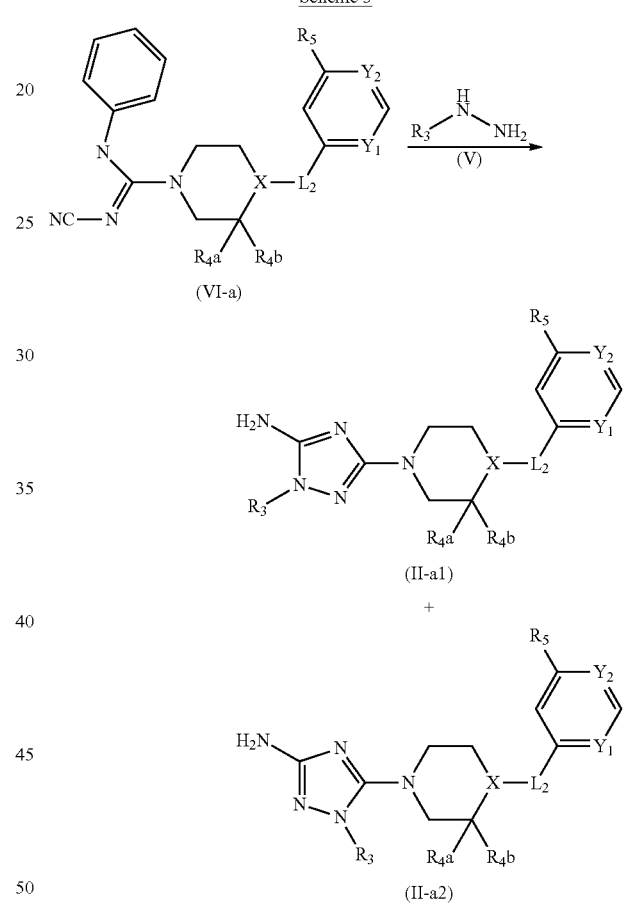

Experimental Procedure 4

An intermediate of formula (VI-a) can be prepared via a nucleophilic substitution reaction between an intermediate of formula (VII) with an appropriate imidate derivative of Formula (VIII) such as, for example diphenyl cyanocarbonimidate according to Scheme 4. The reaction can be performed in a reaction-inert solvent such as, for example, acetonitrile, iso-propanol or dichloromethane. Optionally, the reaction is performed in the presence of a base such as, for example $K_2CO_3$, N,N-diisopropylethylamine

Scheme 4

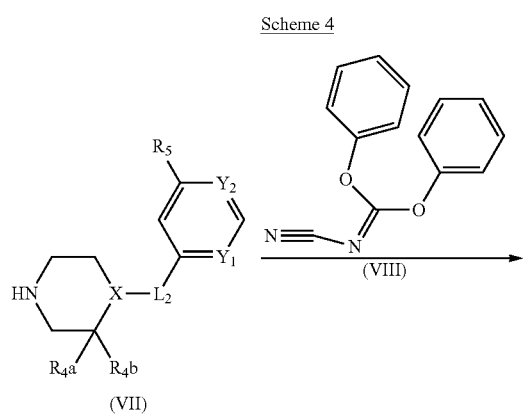

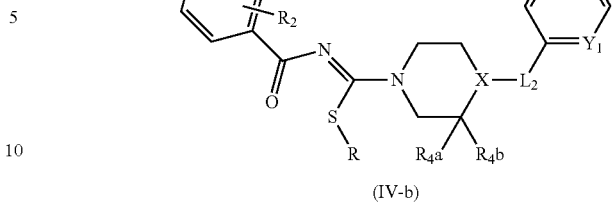

Experimental Procedure 5

An intermediate of formula (IV-b) wherein R represents an alkyl substituent can be prepared via an alkylation reaction between an intermediate of formula (IX-b) with an appropriate alkyl halide of Formula (X) according to Scheme 5. This reaction may be performed in the presence of a suitable base such as, for example, $K_2CO_3$ or sodium hydride. The reaction can be performed in a reaction-inert solvent such as, for example, N,N-dimethylformamide (DMF), acetonitrile, ethanol or acetone. In Scheme 5, halo is defined as Cl, Br or I.

Scheme 5

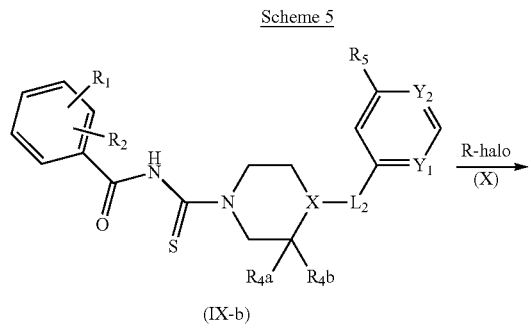

Experimental Procedure 6

An intermediate of formula (IX-b) can be prepared as set out below in Scheme 6:

Scheme 6

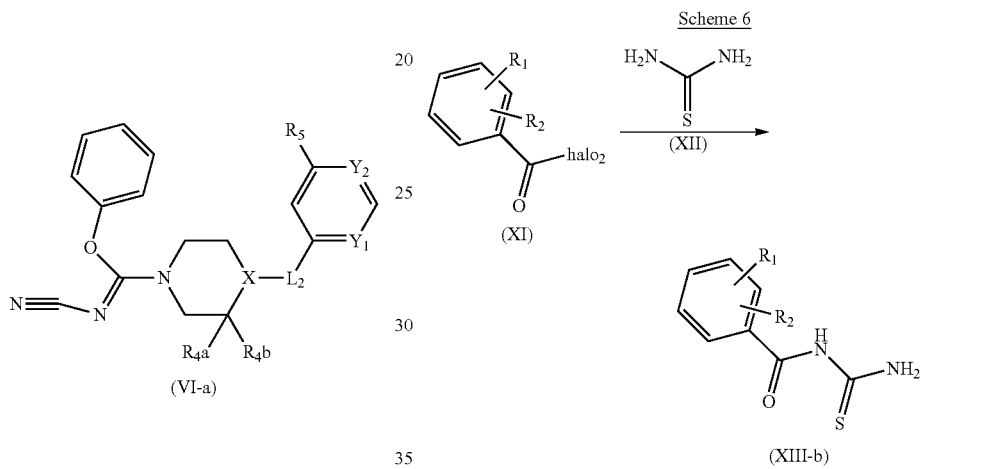

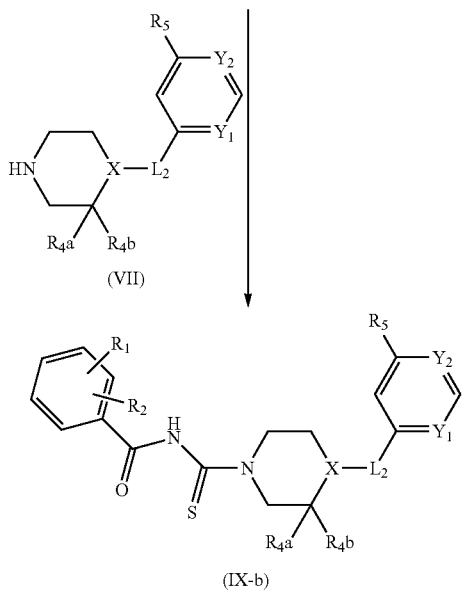

Condensation of a compound of formula (XI) with thiourea or 1,1'-thiocarbonyldiimidazole in a reaction inert solvent, such as, for example acetone, yields an intermediate of formula (XIII-b). Subsequently, an intermediate of formula (XIII-b) is substituted by an intermediate of formula (VII). This reaction step typically can be performed in a reaction inert solvent such as, for example, acetone, to give an intermediate of formula (IX-b). In Scheme 6, halo2 is defined as Cl or Br and all other substituents are defined as mentioned before.

Experimental Procedure 7

Scheme 7

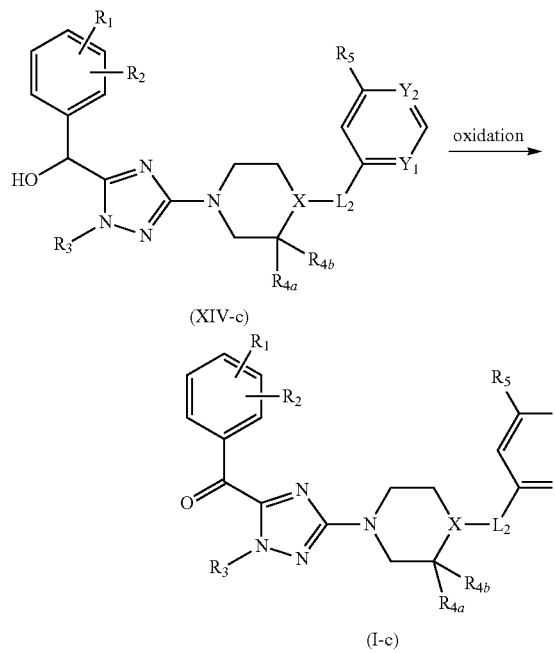

A compound of formula (I) wherein $L_1$ is a CO, hereby named (1-c) can be prepared via an oxidation performed in the presence of an oxidative reagent such as, for example, pyridinium chlorochromate or Dess-Martin reagent. The reaction can be performed in a reaction-inert solvent such as, for example, dichloromethane, acetonitrile or tetrahydrofuran. In Scheme 7, all substituents are defined as mentioned hereinbefore.

Experimental Procedure 8

Scheme 8

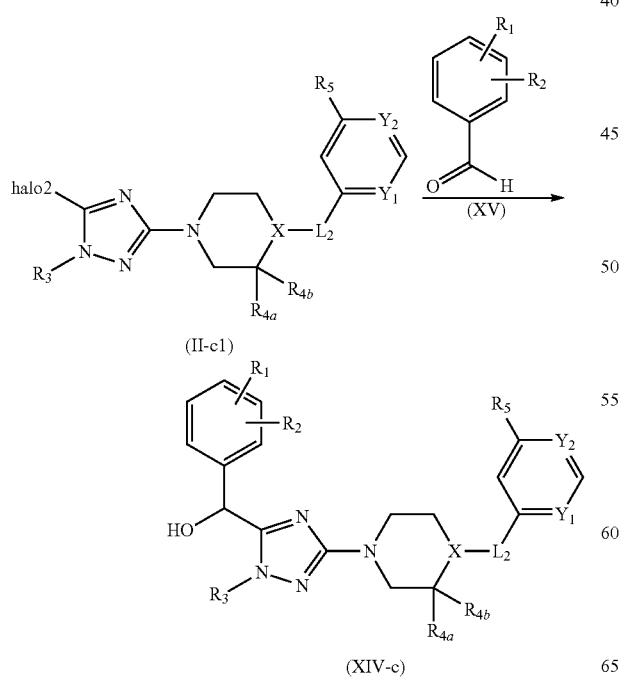

A compound of formula (I) wherein $L_1$ is a CO, hereby named (I-c) can be prepared via an oxidation reaction of an intermediate of formula (XIV-c). This reaction may be performed in the presence of an oxidative reagent such as, for example, pyridinium chlorochromate or Dess-Martin reagent. The reaction can be performed in a reaction-inert solvent such as, for example, dichloromethane, acetonitrile or tetrahydrofuran. In Scheme 7, all substituents are defined as mentioned hereinbefore.

Experimental Procedure 9

Scheme 9

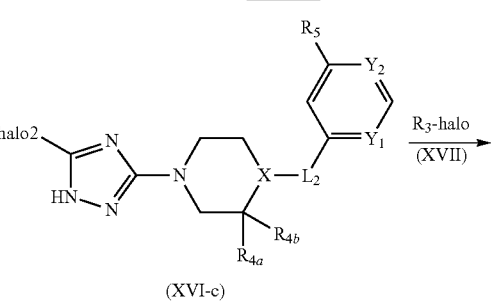

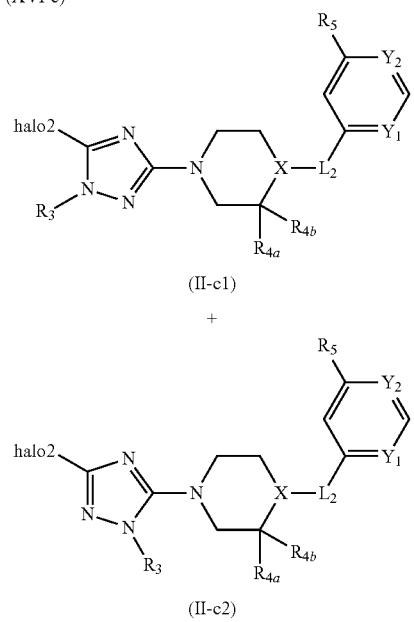

An intermediate of formula (II-c1) can be prepared via an alkylation reaction between an intermediate of formula (XVI-c) with an appropriate alkyl halide of Formula (XVII) according to Scheme 9. This reaction may be performed in the presence of a suitable base such as, for example, $K_2CO_3$ or sodium hydride. The reaction can be performed in a reaction-inert solvent such as, for example, N,N-dimethylformamide (DMF) or tetrahydrofuran. In Scheme 9, halo is defined as Cl, Br or I.

During this reaction, also the regio-isomer of formula (II-c2) is usually formed.

Experimental Procedure 10

Scheme 10

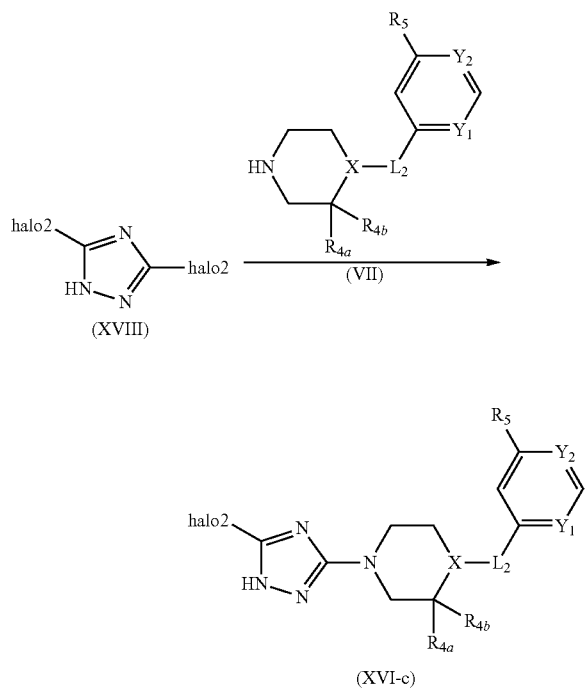

An intermediate of formula (XVI-c) can be prepared via a nucleophilic substitution of an intermediate of formula (XVIII) with an intermediate of formula (VII). This reaction may be performed in the presence of a suitable base such as, for example, $K_2CO_3$ or DIPEA. The reaction can be performed in a reaction-inert solvent such as, for example, n-butanol or acetonitrile. In Scheme 10, halo2 is defined as Cl or Br and all other substituents are defined as mentioned herein before.

Experimental Procedure 11

Scheme 11

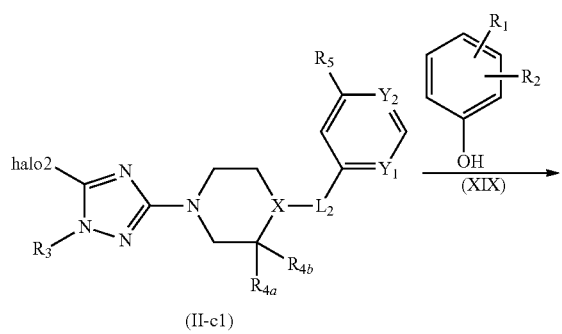

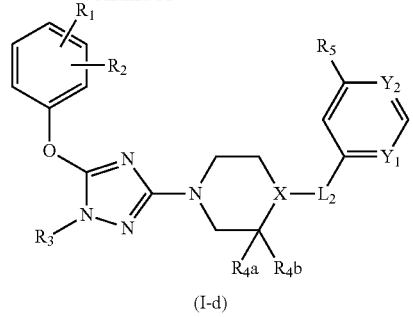

A compound of formula (I) wherein $L_1$ is an O, hereby named (I-d) can be prepared via a nucleophilic substitution of an intermediate of formula (II-c1) with an intermediate of formula (XIX). This reaction may be performed in the presence of a suitable base such as, for example, $K_2CO_3$ or DIPEA. The reaction can be performed in a reaction-inert solvent such as, for example, dichloromethane or acetonitrile. In Scheme 11, halo2 is defined as Cl or Br and all other substituents are defined as mentioned herein before.

Compounds of Formula (III), (V), (VII), (VIII), (X), (XI), (XII), (XV), (XVII), (XVIII) and (XIX) can be obtained commercially or can be easily prepared by those skilled in the art.

In order to obtain the HCl salt forms of the compounds, several procedures known to those skilled in the art can be used. In a typical procedure, for example, the free base can be dissolved in DIPE or $Et_2O$ and subsequently, a 6N HCl solution in 2-propanol or a 1N HCl solution in $Et_2O$ can be added dropwise. The mixture typically is stirred for 10 minutes after which the product can be filtered off. The HCl salt usually is dried in vacuo.

Where necessary or desired, any one or more of the following further steps in any order may be performed:

Compounds of Formula (I), any subgroup thereof, addition salts, solvates, and stereochemical isomeric forms thereof can be converted into further compounds according to the invention using procedures known in the art.

It will be appreciated by those skilled in the art that in the processes described above the functional groups of intermediate compounds may need to be blocked by protecting groups. In case the functional groups of intermediate compounds were blocked by protecting groups, they can be deprotected after a reaction step.

Pharmacology

It has been found that the compounds of the present invention modulate the γ-secretase activity. The compounds according to the invention and the pharmaceutically acceptable compositions thereof therefore may be useful in the treatment or prevention of AD, TBI, dementia pugilistica, MCI, senility, dementia, dementia with Lewy bodies, cerebral amyloid angiopathy, multi-infarct dementia, Down's syndrome, dementia associated with Parkinson's disease and dementia associated with beta-amyloid, preferably AD.

The compounds according to the present invention and the pharmaceutically acceptable compositions thereof may be useful in the treatment or prevention of a disease or condition selected from the group consisting of AD, TBI, MCI, senility, dementia, dementia with Lewy bodies, cerebral amyloid angiopathy, multi-infarct dementia, dementia pugilistica, Down's syndrome, dementia associated with Parkinson's disease and dementia associated with beta-amyloid.

As used herein, the term "modulation of γ-secretase activity" refers to an effect on the processing of APP by the γ-secretase-complex. Preferably it refers to an effect in which the overall rate of processing of APP remains essentially as without the application of said compounds, but in which the relative quantities of the processed products are changed, more preferably in such a way that the amount of the Aβ42-peptide produced is reduced. For example a different Abeta species can be produced (e.g. Abeta-38 or other Abeta peptide species of shorter amino acid sequence instead of Abeta-42) or the relative quantities of the products are different (e.g. the ratio of Abeta-40 to Abeta-42 is changed, preferably increased).

It has been previously shown that the γ-secretase complex is also involved in the processing of the Notch-protein. Notch is a signaling protein which plays a crucial role in developmental processes (e.g. reviewed in Schweisguth F (2004) Curr. Biol. 14, R129). With respect to the use of γ-secretase modulators in therapy, it seems particularly advantageous not to interfere with the Notch-processing activity of the γ-secretase activity in order to avoid putative undesired side-effects. While γ-secretase inhibitors show side effects due to concomitant inhibition of Notch processing, γ-secretase modulators may have the advantage of selectively decreasing the production of highly aggregatable and neurotoxic forms of Aβ, i.e. Aβ42, without decreasing the production of smaller, less aggregatable forms of Aβ, i.e. Aβ38 and without concomitant inhibition of Notch processing. Thus, compounds are preferred which do not show an effect on the Notch-processing activity of the γ-secretase-complex.

As used herein, the term "treatment" is intended to refer to all processes, wherein there may be a slowing, interrupting, arresting, or stopping of the progression of a disease, but does not necessarily indicate a total elimination of all symptoms.

The invention relates to a compound according to the general Formula (I), the stereoisomeric forms thereof and the pharmaceutically acceptable acid or base addition salts and the solvates thereof, for use as a medicament.

The invention also relates to a compound according to the general Formula (I), the stereoisomeric forms thereof and the pharmaceutically acceptable acid or base addition salts and the solvates thereof, for use in the modulation of γ-secretase activity.

The invention also relates to a compound according to the general Formula (I), the stereoisomeric forms thereof and the pharmaceutically acceptable acid or base addition salts and the solvates thereof, for use in the treatment or prevention of diseases or conditions selected from the group consisting of AD, TBI, dementia pugilistica, MCI, senility, dementia, dementia with Lewy bodies, cerebral amyloid angiopathy, multi-infarct dementia, Down's syndrome, dementia associated with Parkinson's disease and dementia associated with beta-amyloid.

In an embodiment, said disease or condition is preferably AD.

The invention also relates to a compound according to the general Formula (I), the stereoisomeric forms thereof and the pharmaceutically acceptable acid or base addition salts and the solvates thereof, for use in the treatment of said diseases.

The invention also relates to a compound according to the general Formula (I), the stereoisomeric forms thereof and the pharmaceutically acceptable acid or base addition salts and the solvates thereof, for the treatment or prevention of said diseases.

The invention also relates to a compound according to the general formula (I), the stereoisomeric forms thereof and the pharmaceutically acceptable acid or base addition salts and the solvates thereof, for the treatment or prevention, in particular treatment, of γ-secretase mediated diseases or conditions.

The invention also relates to the use of a compound according to the general Formula (I), the stereoisomeric forms thereof and the pharmaceutically acceptable acid or base addition salts and the solvates thereof, for the manufacture of a medicament.

The invention also relates to the use of a compound according to the general Formula (I), the stereoisomeric forms thereof and the pharmaceutically acceptable acid or base addition salts and the solvates thereof, for the manufacture of a medicament for the modulation of γ-secretase activity.

The invention also relates to the use of a compound according to the general Formula (I), the stereoisomeric forms thereof and the pharmaceutically acceptable acid or base addition salts and the solvates thereof, for the manufacture of a medicament for the treatment or prevention of any one of the disease conditions mentioned hereinbefore.

The invention also relates to the use of a compound according to the general Formula (I), the stereoisomeric forms thereof and the pharmaceutically acceptable acid or base addition salts and the solvates thereof, for the manufacture of a medicament for the treatment of any one of the disease conditions mentioned hereinbefore.

In the invention, particular preference is given to compounds of Formula (I), or any subgroup thereof with a $IC_{50}$ value for the inhibition of the production of Aβ42-peptide of less than 1000 nM, preferably less than 100 nM, more preferably less than 50 nM, even more preferably less than 20 nM as determined by a suitable assay, such as the assay used in the Examples below.

The compounds of the present invention can be administered to mammals, preferably humans for the treatment or prevention of any one of the diseases mentioned hereinbefore.

In view of the utility of the compound of Formula (I), there is provided a method of treating warm-blooded animals, including humans, suffering from or a method of preventing warm-blooded animals, including humans, to suffer from any one of the diseases mentioned hereinbefore.

Said methods comprise the administration, i.e. the systemic or topical administration, preferably oral administration, of an effective amount of a compound of Formula (I), a stereoisomeric form thereof and a pharmaceutically acceptable addition salt or solvate thereof, to warm-blooded animals, including humans.

The present invention also concerns to the use of a compound of Formula (I) for the modulation of γ-secretase activity resulting in a decrease in the relative amount of Aβ42-peptides produced.

An advantage of the compounds or a part of the compounds of the present invention may be their enhanced CNS-penetration.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. The amount of a compound according to the present invention, also referred to here as the active ingredient, which is required to achieve a therapeutically effect will of course, vary on case-by-case basis, for example with the particular compound, the route of administration, the age and condition of the recipient, and the particular disorder or disease being treated.

A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The compounds of the present invention, that can be suitable to treat or prevent Alzheimer's disease or the symptoms thereof, may be administered alone or in combination with one or more additional therapeutic agents. Combination therapy includes administration of a single pharmaceutical dosage formulation which contains a compound of Formula (I) and one or more additional therapeutic agents, as well as administration of the compound of Formula (I) and each additional therapeutic agents in its own separate pharmaceutical dosage formulation. For example, a compound of Formula (I) and a therapeutic agent may be administered to the patient together in a single oral dosage composition such as a tablet or capsule, or each agent may be administered in separate oral dosage formulations.

While it is possible for the active ingredient to be administered alone, it is preferable to present it as a pharmaceutical composition.

Accordingly, the present invention further provides a pharmaceutical composition comprising a pharmaceutically acceptable carrier and, as active ingredient, a therapeutically effective amount of a compound according to Formula (I).

The carrier or diluent must be "acceptable" in the sense of being compatible with the other ingredients of the composition and not deleterious to the recipients thereof.

For ease of administration, the subject compounds may be formulated into various pharmaceutical forms for administration purposes. The compounds according to the invention, in particular the compounds according to Formula (I), a pharmaceutically acceptable acid or base addition salt thereof, a stereochemically isomeric form thereof, or any subgroup or combination thereof may be formulated into various pharmaceutical forms for administration purposes. As appropriate compositions there may be cited all compositions usually employed for systemically administering drugs.

To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions, for example, may be prepared in which the carrier comprises saline solution, glucose solution or a mixture of saline and glucose solution. Injectable solutions containing compounds of Formula (I) may be formulated in an oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid or base addition salts of compounds of Formula (I) due to their increased water solubility over the corresponding base or acid form, are more suitable in the preparation of aqueous compositions.

It is especially advantageous to formulate the aforementioned pharmaceutical compositions in unit dosage form for ease of administration and uniformity of dosage.

Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Since the compounds according to the invention are potent orally administrable compounds, pharmaceutical compositions comprising said compounds for administration orally are especially advantageous.

In order to enhance the solubility and/or the stability of the compounds of Formula (I) in pharmaceutical compositions, it can be advantageous to employ $\alpha$-, $\beta$- or $\gamma$-cyclodextrins or their derivatives, in particular hydroxyalkyl substituted cyclodextrins, e.g. 2-hydroxypropyl-$\beta$-cyclodextrin or sulfobutyl-$\beta$-cyclodextrin. Also co-solvents such as alcohols may improve the solubility and/or the stability of the compounds according to the invention in pharmaceutical compositions.

Depending on the mode of administration, the pharmaceutical composition will preferably comprise from 0.05 to 99% by weight, more preferably from 0.1 to 70% by weight, even more preferably from 0.1 to 50% by weight of the compound of Formula (I), and, from 1 to 99.95% by weight, more preferably from 30 to 99.9% by weight, even more preferably from 50 to 99.9% by weight of a pharmaceutically acceptable carrier, all percentages being based on the total weight of the composition.

The following examples illustrate the present invention.

EXAMPLES

Hereinafter, the term "DCM" means dichloromethane; "MeOH" means methanol; "LCMS" means Liquid Chromatography/Mass spectrometry; "HPLC" means high-performance liquid chromatography; "sol." means solution; "aq." means aqueous; "r.t." means room temperature; "m.p." means melting point; "RP" means reversed phase; "min" means minute(s); "h" means hour(s); "EtOAc" means ethyl acetate; "eq" means equivalent; "r.m." means reaction mixture(s); "DIPE" means diisopropyl ether; "THF" means tetrahydrofuran; "DMSO" means dimethyl sulfoxide; "DMF" means N,N-dimethyl formamide; "X-Phos" means dicyclohexyl[2',4',6'-tris(1-methylethyl)[1,1'-biphenyl]-2-yl]phosphine; "Pd(dppf)Cl$_2$" means [1,1'-bis(diphenylphosphino)ferrocene]dichloropalladium(II); "DIPEA" means N,N-diisopropylethylamine; "9-BBN" means 9-borabicyclo[3.3.1]nonane; "i-PrOH" means 2-propanol; and "Pd$_2$(dba)$_3$" means tris[μ-[(1,2-η:4,5-η)-(1E,4E)-1,5-diphenyl-1,4-pentadien-3-one]]dipalladium.

A. Preparation of the Intermediates

Example A1

Preparation of Intermediate 1

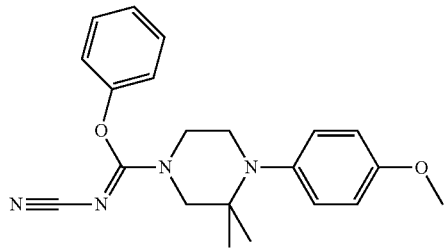 [SMILES: COc1ccc(N2CCN(/C(=N/C#N)Oc3ccccc3)CC2(C)C)cc1]

Diphenyl cyanocarbonimidate (5.3 g, 21.56 mmol) in DCM (50 mL) was added to a sol. of 1-(4-methoxyphenyl)-2,2-dimethylpiperazine (5 g, 21.56 mmol) in DCM (190 mL). The r.m. was stirred at r.t. for 24 h. Water was added and the mixture was extracted with DCM. The separated organic layer was dried (MgSO$_4$), filtered and the solvent was evaporated. The residue was suspended in DIPE, filtered off and dried in the oven. Yield: 6.12 g of intermediate 1 (77%).

Example A2 a) Preparation of Intermediate 2

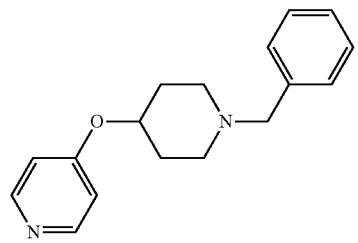 [SMILES: c1ccc(CN2CCC(Oc3ccncc3)CC2)cc1]

Sodium tert-butoxide (5.87 g, 52.28 mmol) was added to 1-benzyl-4-hydroxypiperidine (5 g, 26.14 mmol) in DMSO (12 mL). The r.m. was stirred at r.t. for 1 h. 4-Chloropyridine hydrochloride (4.31 g, 28.75 mmol) was then added and the r.m. was stirred at r.t. for 3 h (slightly exothermic). Water was added and the mixture was extracted with EtOAc. The separated organic layer was dried (MgSO$_4$), filtered and the solvent was evaporated. The residue was purified by flash column chromatography (eluent: DCM/MeOH from 100/0 to 95/5). The product fractions were collected and concentrated in vacuo. Yield: 4.2 g of intermediate 2 (60%).

b) Preparation of Intermediate 3

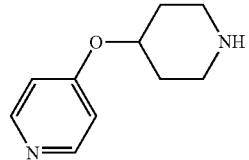 [SMILES: c1cc(OC2CCNCC2)ccn1]

Intermediate 2 was added to a suspension of Pd/C 10% (1 g) MeOH (150 mL) under nitrogen atmosphere. The r.m. was stirred at 25° C. under hydrogen atmosphere. After uptake of H$_2$ (1 eq), the catalyst was filtered off over diatomaceous earth. The filtrate was evaporated. Yield: 2.6 g of intermediate 3 (94%).

c) Preparation of Intermediate 4

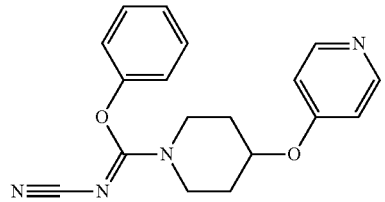 [SMILES: N#C/N=C(\Oc1ccccc1)N1CCC(Oc2ccncc2)CC1]

DIPEA (2.51 mL, 14.59 mmol) then diphenyl cyanocarbonimidate (3.58 g, 14.59 mmol) in DCM (36 mL) were added to a sol. of intermediate 3 (2.6 g, 14.59 mmol) in DCM (126 mL). The r.m. was stirred at r.t. for 4 h. Water was added and the mixture was extracted with DCM. The separated organic layer was dried (MgSO$_4$), filtered and the solvent was evaporated. The residue was purified by flash column chromatography (eluent: DCM/MeOH from 100/0 to 95/5). The product fractions were collected and concentrated in vacuo. Yield: 2.84 g of intermediate 4 (60%).

Example A3 a) Preparation of Intermediate 5

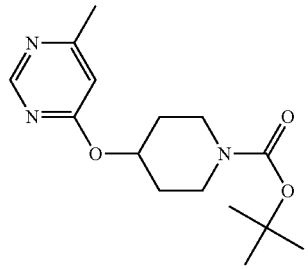 [SMILES: Cc1cc(OC2CCN(C(=O)OC(C)(C)C)CC2)ncn1]

A suspension of 60% NaH in mineral oil (6 g, 150 mmol) was added to 4-hydroxy-piperidine-1-carboxylic acid tert-butyl ester (14.1 g, 70 mmol) in anhydrous THF (120 mL) at 0° C. The r.m. was stirred at 0° C. for 30 min. A sol. of 4-chloro-6-methyl-pyrimidine (9 g, 70 mmol) in anhydrous THF (30 mL) was then added and the r.m. was stirred at r.t. for 24 h. Water was added and the mixture was extracted with DCM. The separated organic layer was dried (MgSO₄), filtered and the solvent was evaporated. The residue was purified by flash column chromatography (eluent: petroleum ether/EtOAc from 10/1 to 1/1). The product fractions were collected and concentrated in vacuo. Yield: 13 g of intermediate 5 (63%).

b) Preparation of Intermediate 6

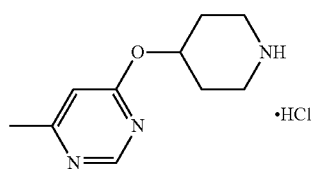

A mixture of intermediate 5 (13 g, 44.3 mmol) in a 4 M sol. of HCl in MeOH (200 mL) was stirred at r.t. for 4 h. The solvent was evaporated. The residue was suspended in DIPE (200 mL), stirred at r.t. for 30 min, filtered off and dried in the oven. Yield: 9.5 g of intermediate 6 (93%)

c) Preparation of Intermediate 7

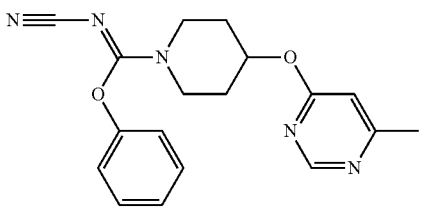 [SMILES: Cc1cc(OC2CCN(/C(=N/C#N)Oc3ccccc3)CC2)ncn1]

DIPEA (3 mL, 17.41 mmol) then diphenyl cyanocarbonimidate (2.14 g, 8.71 mmol) in DCM (21 mL) were added to a sol. of intermediate 6 (2 g, 8.71 mmol) in DCM (77 mL). The r.m. was stirred at r.t. for 1 h. Water was added and the mixture was extracted with DCM. The separated organic layer was dried (MgSO₄), filtered and the solvent was evaporated. The residue was purified by flash column chromatography (eluent: DCM/MeOH from 100/0 to 97.5/2.5). The product fractions were collected and concentrated in vacuo. Yield: 2.09 g of intermediate 7 (71%).

Example A4

Preparation of Intermediate 8

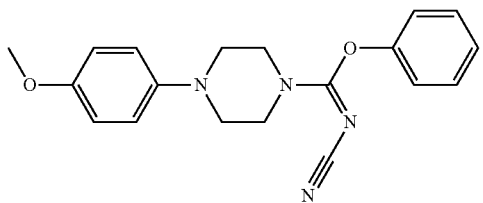 [SMILES: COc1ccc(N2CCN(/C(=N\C#N)Oc3ccccc3)CC2)cc1]

Diphenyl cyanocarbonimidate (2.62 g, 10.68 mmol) in DCM (26 mL) was added to a sol. of 1-(4-methoxyphenyl)-piperazine (5 g, 10.68 mmol) in DCM (94 mL). The r.m. was stirred at r.t. for 24 h. Water was added and the mixture was extracted with DCM. The separated organic layer was dried (MgSO₄), filtered and the solvent was evaporated. Yield: 3.45 g of intermediate 8 (96%).

Example A5

Preparation of Intermediate 9

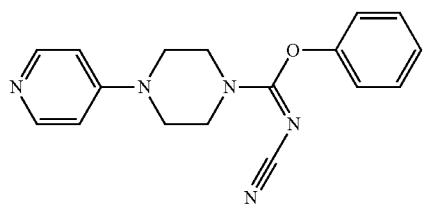 [SMILES: N#C/N=C(/Oc1ccccc1)N1CCN(c2ccncc2)CC1]

Diphenyl cyanocarbonimidate (3.01 g, 12.25 mmol) in DCM (15 mL) was added to a sol. of 1-(pyridin-4-yl)piperazine (2 g, 12.25 mmol) in DCM (32 mL). The r.m. was stirred at r.t. for 1 h. The solvent was evaporated. The residue was purified by flash column chromatography (eluent: DCM/MeOH from 100/0 to 90/10). The product fractions were collected and concentrated in vacuo. The residue was suspended in DIPE, filtered off and dried in the oven. Yield: 3.7 g of intermediate 9 (98%).

Example A6 a) Preparation of Intermediate 10

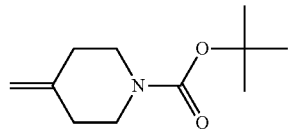

A 2.5 M sol. of n-butyllithium in hexane (30 mL, 75 mmol) was added dropwise to a suspension of methyltriphenyl phosphonium bromide (20 g, 56.0 mmol) in anhydrous THF (130 mL) at −78° C. The r.m. was stirred at −78° C. for 2 h. Then 4-oxo-piperidine-1-carboxylic acid tert-butyl ester (10 g, 50.25 mmol) in anhydrous THF (40 mL) was added dropwise to the r.m. A white suspension was formed during addition. The r.m. was stirred at r.t. for 16 h. Water (10 mL) was added dropwise at 0° C. and the solvent was evaporated. Water (70 mL) was added and the mixture was extracted with EtOAc. The separated organic layer was dried (MgSO₄), filtered and the solvent was evaporated. The residue was purified by flash column chromatography (eluent: petroleum ether/EtOAc 15/1). The product fractions were collected and concentrated in vacuo. Yield: 5.3 g of intermediate 10 (32%, 60% pure).

b) Preparation of Intermediate 11

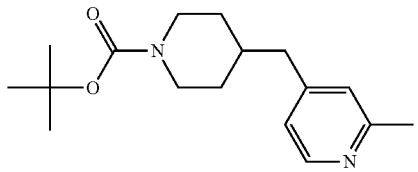 [SMILES: Cc1cc(CC2CCN(C(=O)OC(C)(C)C)CC2)ccn1]

A 0.5 M sol. of 9-BBN (120 mL) in THF was added to a degassed intermediate 10 (11.3 g, 57.36 mmol) and the r.m. was heated at reflux for 1 h. After cooling to r.t., the r.m. was added to a mixture of 4-bromo-2-methyl-pyridine (10.8 g, 63.09 mmol), Pd(dppf)Cl$_2$ (1.259 g, 1.721 mmol) and K$_2$CO$_3$ (23.7 g, 172.1 mmol) in DMF/water 10/1 (250 mL) and the r.m. was heated at 60° C. for 4 h. Then the r.m. was cooled to r.t. and poured into water. The pH was adjusted to 11 by the addition of a 10% aq. NaOH sol. and extracted with EtOAc. The separated organic layer was dried (MgSO$_4$), filtered and the solvent was evaporated. The residue was purified by flash column chromatography (eluent: petroleum ether/EtOAc 20/1). The product fractions were collected and concentrated in vacuo. Yield: 7.6 g of intermediate 11 (46%).

c) Preparation of Intermediate 12

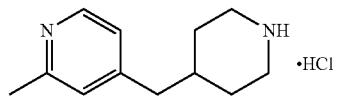

A mixture of intermediate 11 (7.6 g, 20.27 mmol) in a 4M sol. of HCl in MeOH (30 mL) was stirred at r.t. for 4 h. The solvent was evaporated. The residue was suspended in DIPE (200 mL), stirred at r.t. for 30 min, filtered off and dried in the oven. Yield: 5.65 g of intermediate 12 (96%; .HCl)

d) Preparation of Intermediate 13

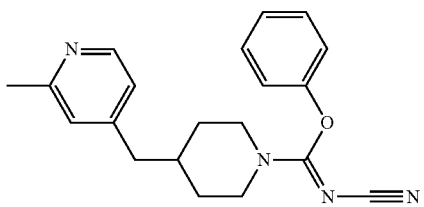 [SMILES: Cc1cc(CC2CCN(/C(=N/C#N)Oc3ccccc3)CC2)ccn1]

DIPEA (1.52 mL, 8.82 mmol) then diphenyl cyanocarbonimidate (1.08 g, 4.41 mmol) in DCM (11 mL) were added to a sol. of intermediate 12 (1 g, 4.41 mmol) in DCM (39 mL). The r.m. was stirred at r.t. for 1 h. The solvent was evaporated. Yield: 0.5 g of intermediate 13 (34%).

Example A7

Preparation of Intermediate 14

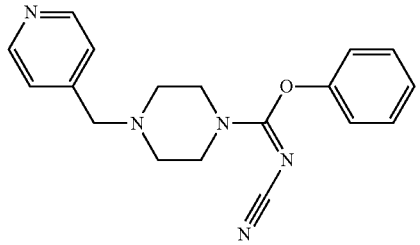 [SMILES: N#C/N=C(/Oc1ccccc1)N1CCN(Cc2ccncc2)CC1]

Diphenyl cyanocarbonimidate (2.77 g, 11.28 mmol) in DCM (15 mL) was added to a sol. of 1-(4-pyridylmethyl)-piperazine (2 g, 11.28 mmol) in DCM (16 mL). The r.m. was stirred at r.t. for 1 h. The solvent was evaporated. The residue was purified by flash column chromatography (eluent: DCM/MeOH from 100/0 to 95/5). The product fractions were collected and concentrated in vacuo. The residue was suspended in DIPE, filtered off and dried in the oven. Yield: 3.5 g of intermediate 14 (96%)

Example A8 a) Preparation of Intermediate 15

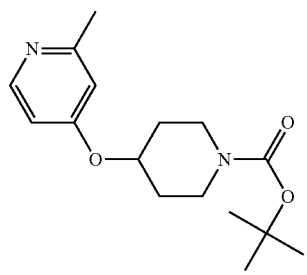 [SMILES: Cc1cc(OC2CCN(C(=O)OC(C)(C)C)CC2)ccn1]

Sodium tert-butoxide (8.8 g, 78.4 mmol) was added to 4-hydroxy-piperidine-1-carboxylic acid tert-butyl ester (7.89 g, 39.2 mmol) in DMSO (39 mL). The r.m. was stirred at r.t. for 1 h. 4-Chloro-2-picoline (5 g, 39.2 mmol) was then added and the r.m. was stirred at 50° C. for 48 h. Then, the r.m. was cooled to r.t. Water was added and the mixture was extracted with EtOAc. The separated organic layer was washed with a sol. of NaHCO$_3$ and brine, was dried (MgSO$_4$), filtered and the solvent was evaporated. The residue was purified by flash column chromatography (eluent: DCM/MeOH from 100/0 to 98/2). The product fractions were collected and concentrated in vacuo. Yield: 8.8 g of intermediate 15 (77%).

b) Preparation of Intermediate 16

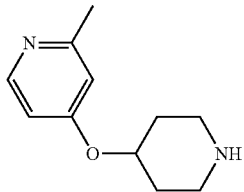

A 6 N sol. of HCl in 2-propanol (8.62 mL, 51.7 mmol) was added to a sol. of intermediate 15 (2.5 g, 8.55 mmol) in 2-propanol (52 mL) was stirred at r.t. for 30 min. The solvent was evaporated. The residue was suspended in CH$_3$CN. The product was filtered off and dissolved in water. The base was set free with an aq. sol. K$_2$CO$_3$ and the mixture extracted with DCM. The organic phase was separated, dried (MgSO$_4$), filtered and the solvent was evaporated. The product was used in the next step without further purification. Yield: 1.52 g of intermediate 16 (93%).

c) Preparation of Intermediate 17

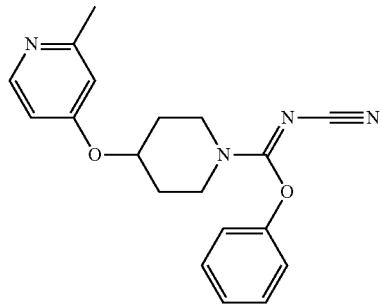 [SMILES: Cc1cc(OC2CCN(/C(=N/C#N)Oc3ccccc3)CC2)ccn1]

Diphenyl cyanocarbonimidate (1.28 g, 5.2 mmol) in DCM (15 mL) was added to a sol. of intermediate 16 (2 g, 5.2 mmol) in DCM (5 mL). The r.m. was stirred at r.t. for 1 h. The solvent was evaporated. The residue was purified by flash column chromatography (eluent: DCM/MeOH from 100/0 to 95/5). The product fractions were collected and concentrated in vacuo. Yield: 1.75 g of intermediate 17 (100%).

Example A9 a) Preparation of Intermediate 18

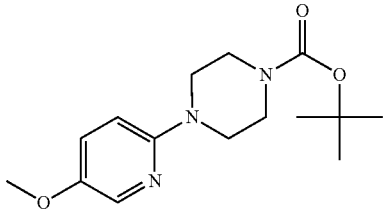 [SMILES: COc1ccc(N2CCN(C(=O)OC(C)(C)C)CC2)nc1]

2-Bromo-5-methoxypyridine (2 g, 10.64 mmol), Cs$_2$CO$_3$ (10.4 g, 31.91 mmol), X-Phos (1.12 g, 2.34 mmol) and Pd$_2$(dba)$_3$ (974 mg, 1.06 mmol), were added to a sol. of piperazine-1-carboxylic acid tert-butyl ester (3.96 g, 21.27 mmol) in 2-methyl-2-propanol (120 mL) under a N$_2$ atmosphere. The r.m. was heated at 100° C. for 48 h. Then, the r.m. was cooled to r.t., water was added and the mixture was extracted with DCM. The combined organic layers were dried (MgSO$_4$), filtered and concentrated in vacuo. The residue was purified by flash column chromatography (eluent: DCM/MeOH from 100/0 to 98/2). The product fractions were collected and concentrated in vacuo. Then the residue was repurified by RP preparative HPLC [RP Vydac Denali C18-10 μm, 250 g, 5 cm); mobile phase: a gradient of (0.25% NH$_4$HCO$_3$ sol. in water)/MeOH/CH$_3$CN)]. The product fractions were collected and concentrated in vacuo. Yield: 100 mg of intermediate 18 (3.2%).

b) Preparation of Intermediate 19

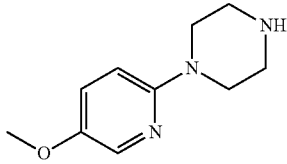

A 6 N sol. of HCl in 2-propanol (2 mL, 12 mmol) was added to a sol. of intermediate 18 (100 mg, 0.34 mmol) in 2-propanol (2 mL) was stirred at r.t. for 16 h. The solvent was evaporated. The residue was dissolved in DCM and washed with a 1 N sol. of NaOH. The separated organic layer was washed with a sol. of NaHCO$_3$ and brine, was dried (MgSO$_4$), filtered and the solvent was evaporated. The product was used in the next step without further purification. Yield: 53 mg of intermediate 19 (80%).

c) Preparation of Intermediate 20

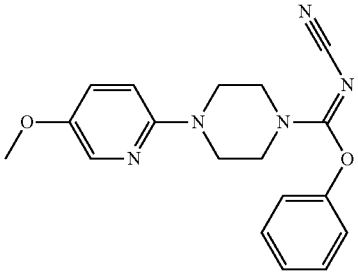 [SMILES: COc1ccc(N2CCN(/C(=N\C#N)Oc3ccccc3)CC2)nc1]

Diphenyl cyanocarbonimidate (65 mg, 0.27 mmol) in DCM (15 mL) was added to a sol. of intermediate 19 (53 mg, 0.27 mmol) in DCM (38 mL). The r.m. was stirred at r.t. for 1.5 h. The solvent was evaporated. The product was used in the next step without further purification. Yield: 120 mg of intermediate 20 (quantitative).

Example A10

Preparation of Intermediate 21 and Intermediate 22 (Regioisomers)

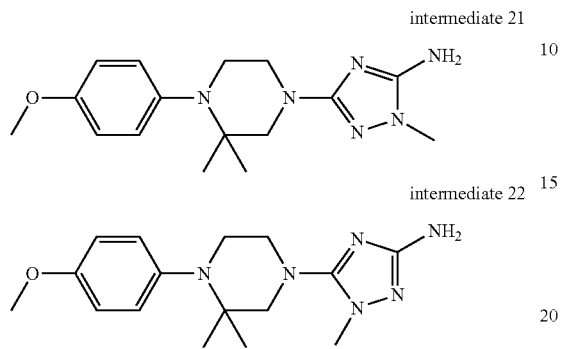

Methylhydrazine (0.14 mL, 2.68 mmol) was added to a sol. of intermediate 1 (0.98 g, 2.68 mmol) in 2-propanol (16 mL). The r.m. was stirred at r.t. for 16 h. The solvent was evaporated. The residue was purified by flash column chromatography (eluent: DCM/MeOH from 100/0 to 97/3). The product fractions were collected and concentrated in vacuo. Yield: 270 mg of intermediate 21 (32%) and 157 mg of intermediate 22 (18%).

Example A11

Preparation of Intermediate 23 and Intermediate 24 (Regioisomers)

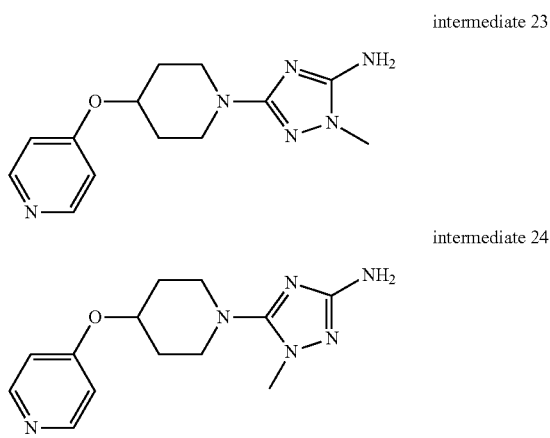

Methylhydrazine (0.47 mL, 8.69 mmol) was added to a sol. of intermediate 4 (2.8 g, 8.69 mmol) in 2-propanol (50 mL). The r.m. was heated at reflux for 6 h. The solvent was evaporated. The residue was suspended in CH$_3$CN, filtered off and dried in the oven. Yield: 1.67 g containing 59% of intermediate 23 and 34% of intermediate 24.

Example A12

Preparation of Intermediate 25 and Intermediate 26 (Regioisomers)

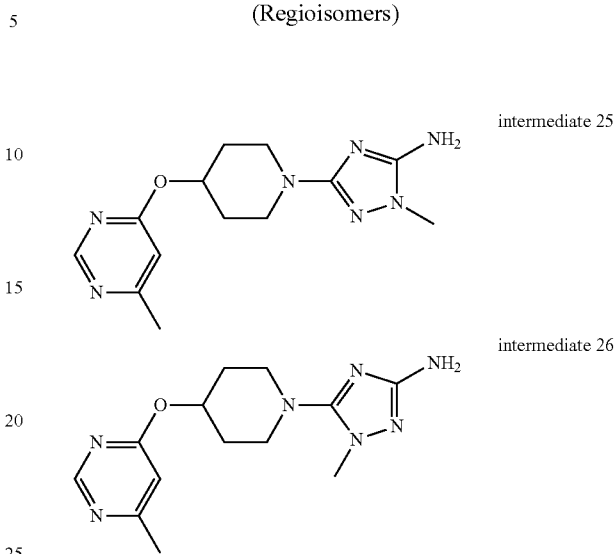

Methylhydrazine (0.34 mL, 6.19 mmol) was added to a sol. of intermediate 7 (2.09 g, 6.19 mmol) in 2-propanol (35 mL). The r.m. was heated at reflux for 6 h. The solvent was evaporated. The residue was purified by flash column chromatography (eluent: DCM/MeOH from 100/0 to 95/5). The product fractions were collected and concentrated in vacuo. The residue was suspended in DIPE, filtered off and dried in the oven. Yield: 179 mg of intermediate 25 (10%) and 159 mg of intermediate 26 (9%).

Example A13

Preparation of Intermediate 27 and Intermediate 28 (Regioisomers)

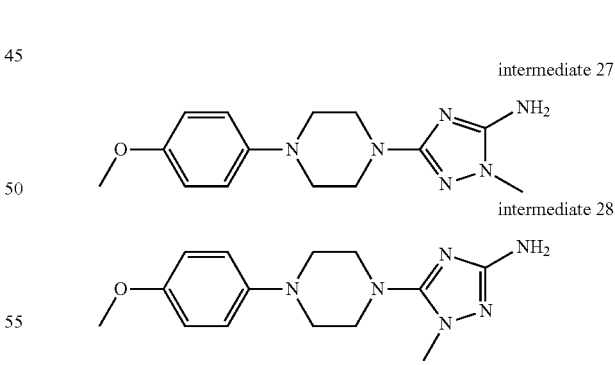

Methylhydrazine (0.55 mL, 10.17 mmol) was added to a sol. of intermediate 8 (3.42 g, 10.17 mmol) in 2-propanol (58 mL). The r.m. was heated at reflux for 6 h. The solvent was evaporated. The residue was purified by flash column chromatography (eluent: DCM/MeOH from 100/0 to 95/5). The product fractions were collected and concentrated in vacuo. The residue was suspended in DIPE, filtered off and dried in the oven. Yield: 510 mg of intermediate 27 (17%) and 720 mg of intermediate 28 (24%).

Example A14

Preparation of Intermediate 29 and Intermediate 30 (Regioisomers)

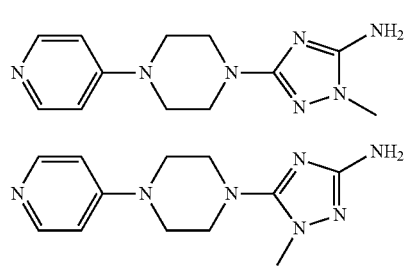

intermediate 29 intermediate 30

Methylhydrazine (0.71 mL, 13.01 mmol) was added to a sol. of intermediate 9 (4 g, 13.01 mmol) in 2-propanol (75 mL). The r.m. was heated at reflux for 16 h. Additional methylhydrazine (0.35 mL, 6.50 mmol) was added and the r.m. was heated at reflux for 16 h. The solvent was evaporated. The residue was crystallized from $CH_3CN$, filtered off and dried in the oven. Yield: 2.9 g containing a mixture of intermediate 29 and intermediate 30, that was used as such in the next reaction step.

Example A15

Preparation of Intermediate 31 and Intermediate 32 (Regioisomers)

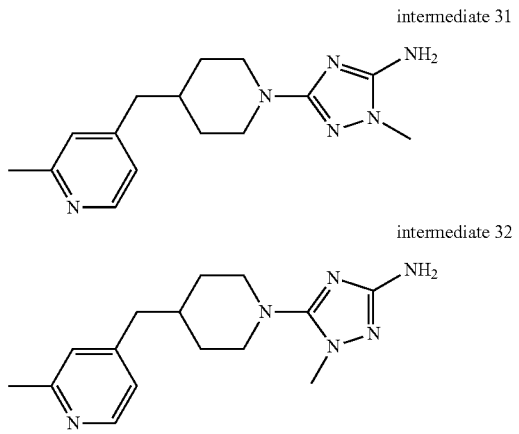

intermediate 31 intermediate 32

Methylhydrazine (0.081 mL, 1.5 mmol) was added to a sol. of intermediate 13 (500 mg, 1.5 mmol) in 2-propanol (8 mL). The r.m. was heated at reflux for 6 h. The solvent was evaporated. The product was used in the next step without further purification. Yield: 510 mg containing 56% of intermediate 31 and 32% of intermediate 32.

Example A16

Preparation of Intermediate 33 and Intermediate 34 (Regioisomers)

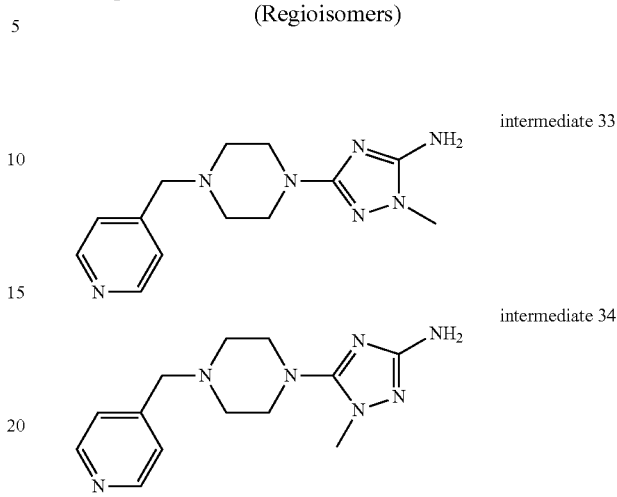

intermediate 33 intermediate 34

Methylhydrazine (0.59 mL, 10.89 mmol) was added to a sol. of intermediate 14 (3.5 g, 10.89 mmol) in 2-propanol (62 mL). The r.m. was heated at reflux for 16 h. Additional methylhydrazine (0.59 mL, 10.89 mmol) was added and the r.m. was heated at reflux for 16 h. The solvent was evaporated. The residue was crystallized from $CH_3CN$, filtered off and dried in the oven. Yield: 1.1 g of intermediate 33 (37%). The regioisomer of intermediate 33 (intermediate 34) was also formed during this reaction, but was not isolated.

Example A17

Preparation of Intermediate 35 and Intermediate 36 (Regioisomers)

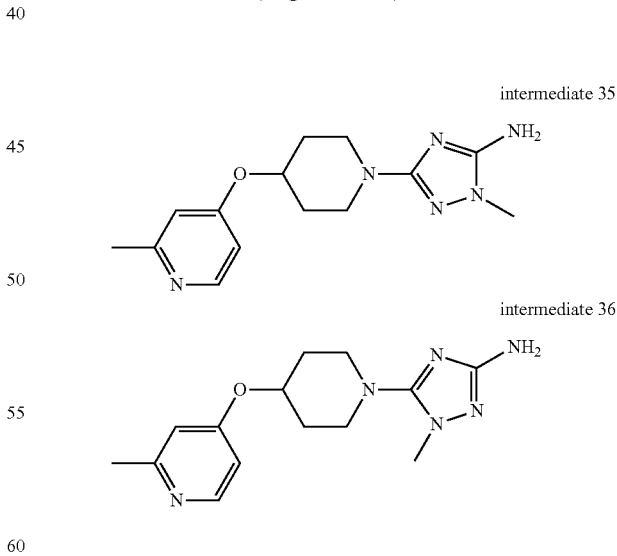

intermediate 35 intermediate 36

Methylhydrazine (0.28 mL, 5.2 mmol) was added to a sol. of intermediate 17 (1.75 g, 5.2 mmol) in 2-propanol (30 mL). The r.m. was heated at reflux for 16 h. The solvent was evaporated. The residue was crystallized from $CH_3CN$, filtered off and dried in the oven. Yield: 361 mg of intermediate 35 (24%). The regioisomer of intermediate 35 (intermediate 36) was also formed during this reaction, but was not isolated.

Example A18

Preparation of Intermediate 37 and Intermediate 38 (Regioisomers)

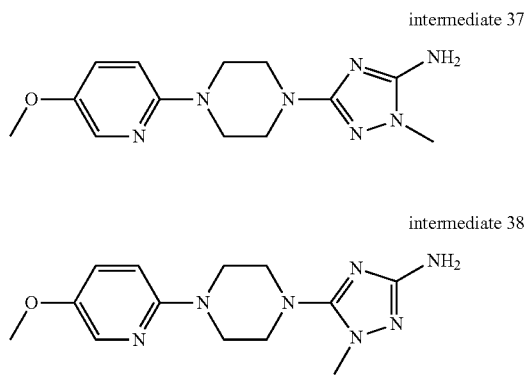

intermediate 37 intermediate 38

Methylhydrazine (0.019 mL, 0.36 mmol) was added to a sol. of intermediate 20 (120 mg, 0.36 mmol) in 2-propanol (2 mL). The r.m. was heated at r.t. for 16 h. The solvent was evaporated. The residue was purified by flash column chromatography (eluent: DCM/MeOH from 100/0 to 97/3). The product fractions were collected and concentrated in vacuo. Yield: 25 mg of intermediate 37 (24%). The regioisomer of intermediate 37 (intermediate 38) was also formed during this reaction, but was not isolated.

Example A19

Preparation of Intermediate 39

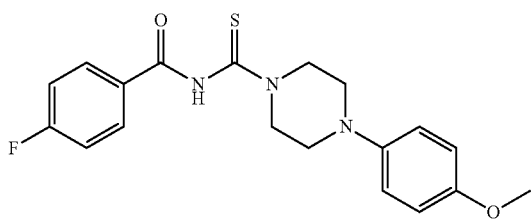 [SMILES: COc1ccc(N2CCN(C(=S)NC(=O)c3ccc(F)cc3)CC2)cc1]

4-Fluorobenzoyl chloride (5 g, 31.53 mmol) was added to a mixture of thiourea (2.52 g, 33.1 mmol) in acetone (100 mL) and the r.m. was stirred at r.t. for 1 h. Then 1-(4-methoxyphenyl)-piperazine (5.76 g, 29.96 mmol) was added and the r.m. was stirred at r.t. for 1 h. The r.m. was poured into ice water. The precipitate was filtered off and dried. Yield: 5.68 g of intermediate 39 (48%).

Example A20

Preparation of Intermediate 40

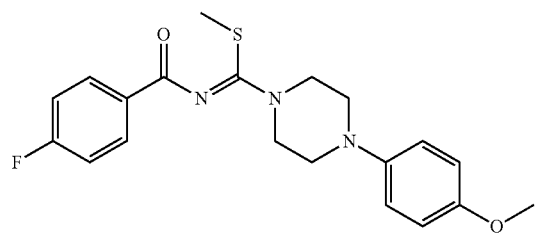 [SMILES: COc1ccc(N2CCN(/C(=N/C(=O)c3ccc(F)cc3)SC)CC2)cc1]

$K_2CO_3$ (0.74 g, 5.35 mmol) was added to a mixture of intermediate 39 (2 g, 5.36 mmol) in acetone (20 mL). The r.m. was stirred at r.t. for 30 min. Iodomethane (0.84 g, 5.89 mmol) was added. The r.m. was stirred at r.t. for 1 h. The solvent was evaporated. Water was added and the mixture was extracted with DCM. The combined organic layers were dried ($MgSO_4$), filtered and concentrated in vacuo. Yield: 2.07 g of intermediate 40 (quantitative).

B. Preparation Of the Compounds

Example B1

Preparation of Compound 1

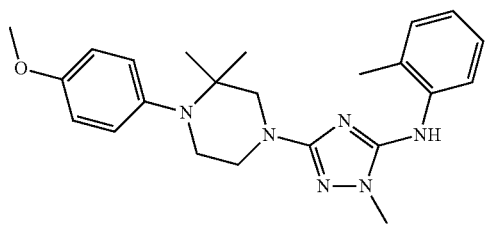 [SMILES: COc1ccc(N2CCN(c3nc(Nc4ccccc4C)n(C)n3)CC2(C)C)cc1]

2-Bromotoluene (0.076 mL, 0.63 mmol), $Cs_2CO_3$ (618 mg, 1.9 mmol), X-Phos (73 mg, 0.13 mmol) and $Pd_2(dba)_3$ (58 mg, 0.063 mmol), were added to a sol. of intermediate 21 (200 mg, 0.63 mmol) in 2-methyl-2-propanol (14 mL) under a $N_2$ atmosphere. The r.m. was heated at 100° C. for 16 h. Then, the r.m. was cooled to r.t., water was added and the r.m. was extracted with DCM. The combined organic layers were dried ($MgSO_4$), filtered and concentrated in vacuo. The residue was purified by flash column chromatography (eluent: DCM/MeOH from 100/0 to 95/5). The product fractions were collected and concentrated in vacuo. The residue was triturated with DIPE, filtered off and dried. Yield: 120 mg of compound 1 (47%).

Example B2

Preparation of Compound 2

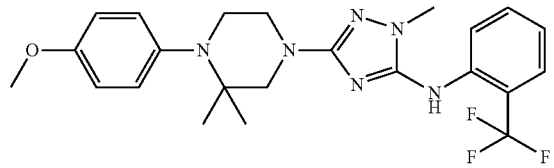 [SMILES: COc1ccc(N2CCN(c3nc(Nc4ccccc4C(F)(F)F)n(C)n3)CC2(C)C)cc1]

2-Bromobenzotrifluoride (0.086 mL, 0.63 mmol), Cs$_2$CO$_3$ (618 mg, 1.9 mmol), X-Phos (73 mg, 0.13 mmol) and Pd$_2$(dba)$_3$ (58 mg, 0.063 mmol), were added to a sol. of intermediate 21 (200 mg, 0.63 mmol) in 2-methyl-2-propanol (14 mL) under a N$_2$ atmosphere. The r.m. was heated at 100° C. for 16 h. Then, the r.m. was cooled to r.t., water was added and the r.m. was extracted with DCM. The combined organic layers were dried (MgSO$_4$), filtered and concentrated in vacuo. The residue was purified by RP preparative HPLC [RP Vydac Denali C18-10 µm, 250 g, 5 cm); mobile phase: a gradient of (0.25% NH$_4$HCO$_3$ Sol. in water)/MeOH)]. The product fractions were collected and concentrated in vacuo. Then the residue was repurified by RP preparative HPLC [RP Vydac Denali C18-10 µm, 250 g, 5 cm); mobile phase: a gradient of (0.15% formic acid solution in water, MeOH/CH$_3$CN]. The product fractions were collected and concentrated in vacuo. Yield: 44 mg of compound 2 (15%).

Example B3

Preparation of Compound 3

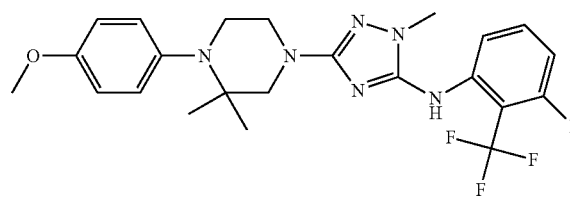

1-Bromo-3-fluoro-2-trifluoromethyl-benzene (0.095 mL, 0.95 mmol), Cs$_2$CO$_3$ (618 mg, 1.9 mmol), X-Phos (73 mg, 0.13 mmol) and Pd$_2$(dba)$_3$ (58 mg, 0.063 mmol), were added to a sol. of intermediate 21 (200 mg, 0.63 mmol) in 2-methyl-2-propanol (14 mL) under a N$_2$ atmosphere. The r.m. was heated at 100° C. for 16 h. Then, the r.m. was cooled to r.t., water was added and the r.m. was extracted with DCM. The combined organic layers were dried (MgSO$_4$), filtered and concentrated in vacuo. The residue was purified by flash column chromatography (eluent: DCM/MeOH from 100/0 to 95/5). The product fractions were collected and concentrated in vacuo. The residue was suspended in DIPE, filtered off. The residue was repurified by RP preparative HPLC [RP Vydac Denali C18-10 µm, 250 g, 5 cm); mobile phase: a gradient of (0.25% NH$_4$HCO$_3$ sol. in water/MeOH)]. The product fractions were collected and concentrated in vacuo. Then the residue was repurified by RP preparative HPLC [RP Vydac Denali C18-10 µm, 250 g, 5 cm); mobile phase: a gradient of (0.15% formic acid solution in water, MeOH/CH$_3$CN]. The product fractions were collected and concentrated in vacuo. Yield: 30 mg of compound 3 (10%).

Example B4

Preparation of Compound 4

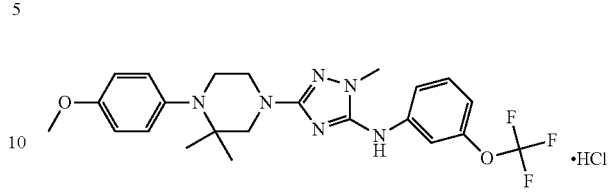

1-Bromo-3-trifluoromethoxy-benzene (0.093 mL, 0.95 mmol), Cs$_2$CO$_3$ (618 mg, 1.9 mmol), X-Phos (73 mg, 0.13 mmol) and Pd$_2$(dba)$_3$ (58 mg, 0.063 mmol), were added to a sol. of intermediate 21 (200 mg, 0.63 mmol) in 2-methyl-2-propanol (14 mL) under a N$_2$ atmosphere. The r.m. was heated at 100° C. for 16 h. Then, the r.m. was cooled to r.t., water was added and the r.m. was extracted with DCM. The combined organic layers were dried (MgSO$_4$), filtered and concentrated in vacuo. The residue was purified by flash column chromatography (eluent: DCM/MeOH from 100/0 to 95/5). The product fractions were collected and concentrated in vacuo. The residue was suspended in DIPE, filtered off. The residue was suspended in 2-propanol and treated with a 6 N HCl sol. in 2-propanol. The resulting precipitate was collected by filtration and dried. Yield: 130 mg of compound 4 (41%) as HCl salt.

Example B5

Preparation of Compound 5

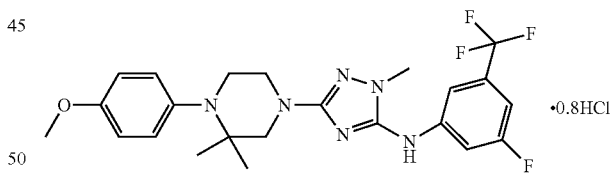

1-Bromo-3-fluoro-5-trifluoromethyl-benzene (230 mg, 0.95 mmol), Cs$_2$CO$_3$ (618 mg, 1.9 mmol), X-Phos (73 mg, 0.13 mmol) and Pd$_2$(dba)$_3$ (58 mg, 0.063 mmol), were added to a sol. of intermediate 21 (200 mg, 0.63 mmol) in 2-methyl-2-propanol (14 mL) under a N$_2$ atmosphere. The r.m. was heated at 100° C. for 16 h. Then, the r.m. was cooled to r.t., water was added and the r.m. was extracted with DCM. The combined organic layers were dried (MgSO$_4$), filtered and concentrated in vacuo. The residue was purified by flash column chromatography (eluent: DCM/MeOH from 100/0 to 95/5). The product fractions were collected and concentrated in vacuo. The residue was suspended in DIPE and treated with a 6 N HCl sol. in 2-propanol. The resulting precipitate was collected by filtration and dried. Yield: 121 mg of compound 5 (38%) as HCl salt (.0.8HCl).

Example B6

Preparation of Compound 6

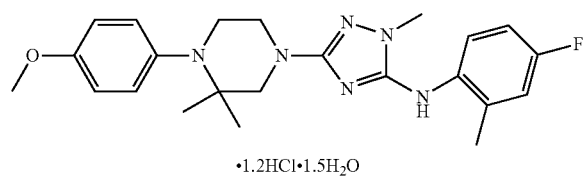

•1.2HCl•1.5H₂O

1-Bromo-4-fluoro-2-methyl-benzene (0.12 mL, 0.95 mmol), Cs₂CO₃ (618 mg, 1.9 mmol), X-Phos (73 mg, 0.13 mmol) and Pd₂(dba)₃ (58 mg, 0.063 mmol), were added to a sol. of intermediate 21 (200 mg, 0.63 mmol) in 2-methyl-2-propanol (14 mL) under a N₂ atmosphere. The r.m. was heated at 100° C. for 16 h. Then, the r.m. was cooled to r.t., water was added and the r.m. was extracted with DCM. The combined organic layers were dried (MgSO₄), filtered and concentrated in vacuo. The residue was purified by flash column chromatography (eluent: DCM/MeOH from 100/0 to 95/5). The product fractions were collected and concentrated in vacuo. The residue was suspended in DIPE and treated with a 6 N HCl sol. in 2-propanol. The resulting precipitate was collected by filtration and dried. Yield: 115 mg of compound 6 (37%) as HCl salt (.1.2HCl. 1.5H₂O).

Example B7

Preparation of Compound 7 and Compound 7a compound 7

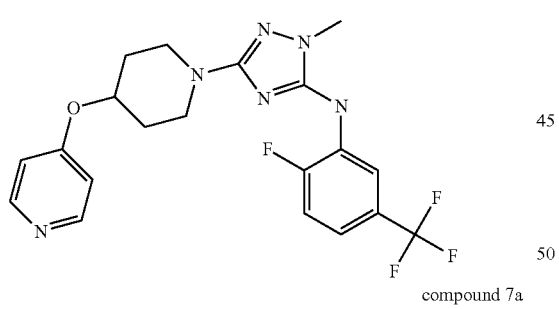

compound 7a

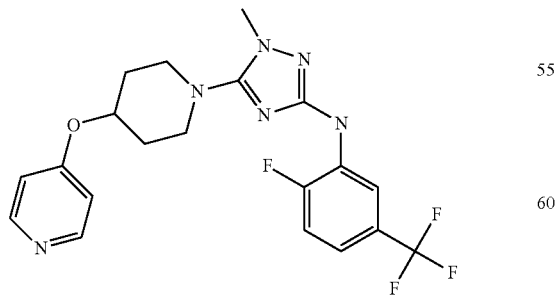

3-Bromo-4-fluorobenzotrifluoride (0.39 mL, 2.73 mmol), Cs₂CO₃ (1.78 g, 5.47 mmol), X-Phos (211 mg, 0.36 mmol) and Pd₂(dba)₃ (167 mg, 0.18 mmol), were added to a mixture of intermediate 23 and intermediate 24 (500 mg, 1.82 mmol) in 2-methyl-2-propanol (41 mL) under a N₂ atmosphere. The r.m. was heated at 100° C. for 16 h. Then, the r.m. was cooled to r.t., water was added and the r.m. was extracted with DCM. The combined organic layers were dried (MgSO₄), filtered and concentrated in vacuo. The residue was purified by flash column chromatography (eluent: DCM/MeOH from 100/0 to 95/5). The product fractions were collected and concentrated in vacuo. Yield: 69 mg of compound 7 (9%) and 108 mg of compound 7a (14%; regioisomer of compound 7).

Example B8

Preparation of Compound 8

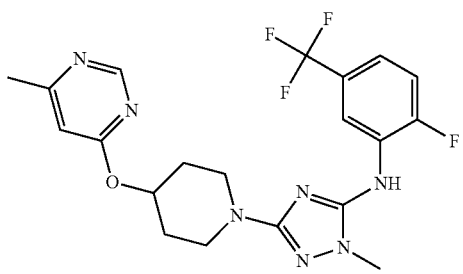 [SMILES: Cc1cc(OC2CCN(c3nc(Nc4cc(C(F)(F)F)ccc4F)n(C)n3)CC2)ncn1]

3-Bromo-4-fluorobenzotrifluoride (0.086 mL, 0.63 mmol), Cs₂CO₃ (618 mg, 1.9 mmol), X-Phos (73 mg, 0.13 mmol) and Pd₂(dba)₃ (58 mg, 0.063 mmol), were added to a sol. of intermediate 25 (200 mg, 0.63 mmol) in 2-methyl-2-propanol (14 mL) under a N₂ atmosphere. The r.m. was heated at 100° C. for 16 h. Then, the r.m. was cooled to r.t., water was added and the r.m. was extracted with DCM. The combined organic layers were dried (MgSO₄), filtered and concentrated in vacuo. The residue was purified by flash column chromatography (eluent: DCM/MeOH from 100/0 to 95/5). The product fractions were collected and concentrated in vacuo. The residue was triturated with DIPE, filtered off and dried. Yield: 79 mg of compound 8 (28%).

Example B9

Preparation of Compound 9

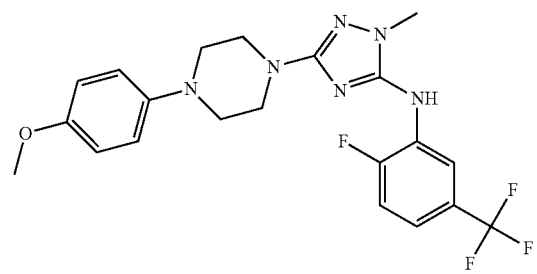 [SMILES: COc1ccc(N2CCN(c3nc(Nc4cc(C(F)(F)F)ccc4F)n(C)n3)CC2)cc1]

3-Bromo-4-fluorobenzotrifluoride (0.22 mL, 1.56 mmol), Cs₂CO₃ (1.02 g, 3.12 mmol), X-Phos (120 mg, 0.21 mmol) and Pd₂(dba)₃ (95 mg, 0.1 mmol), were added to a sol. of intermediate 27 (300 mg, 1.04 mmol) in 2-methyl-2-propanol (23 mL) under a $N_2$ atmosphere. The r.m. was heated at 100° C. for 16 h. Then, the r.m. was cooled to r.t., water was added and the r.m. was extracted with DCM. The combined organic layers were dried ($MgSO_4$), filtered and concentrated in vacuo. The residue was purified by flash column chromatography (eluent: DCM/MeOH from 100/0 to 95/5). The product fractions were collected and concentrated in vacuo. The residue was triturated with DIPE, filtered off and dried. Yield: 120 mg of compound 9 (25%).

Example B10

Preparation of Compound 10 and Compound 10a column chromatography (eluent: DCM/MeOH from 100/0 to 95/5). The product fractions were collected and concentrated in vacuo. The residue was repurified by RP preparative HPLC [RP Vydac Denali C18-10 µm, 250 g, 5 cm); mobile phase: a gradient of (0.25% $NH_4HCO_3$ sol. in water/$CH_3CN$)]. The product fractions were collected and concentrated in vacuo. The residue was crystallized from DIPE, filtered off and dried. Yield: 112 mg of compound 10 (28%) and 80 mg of compound 10a (20%; regioisomer of compound 10).

Example B11

Preparation of Compound 11 and Compound 11a

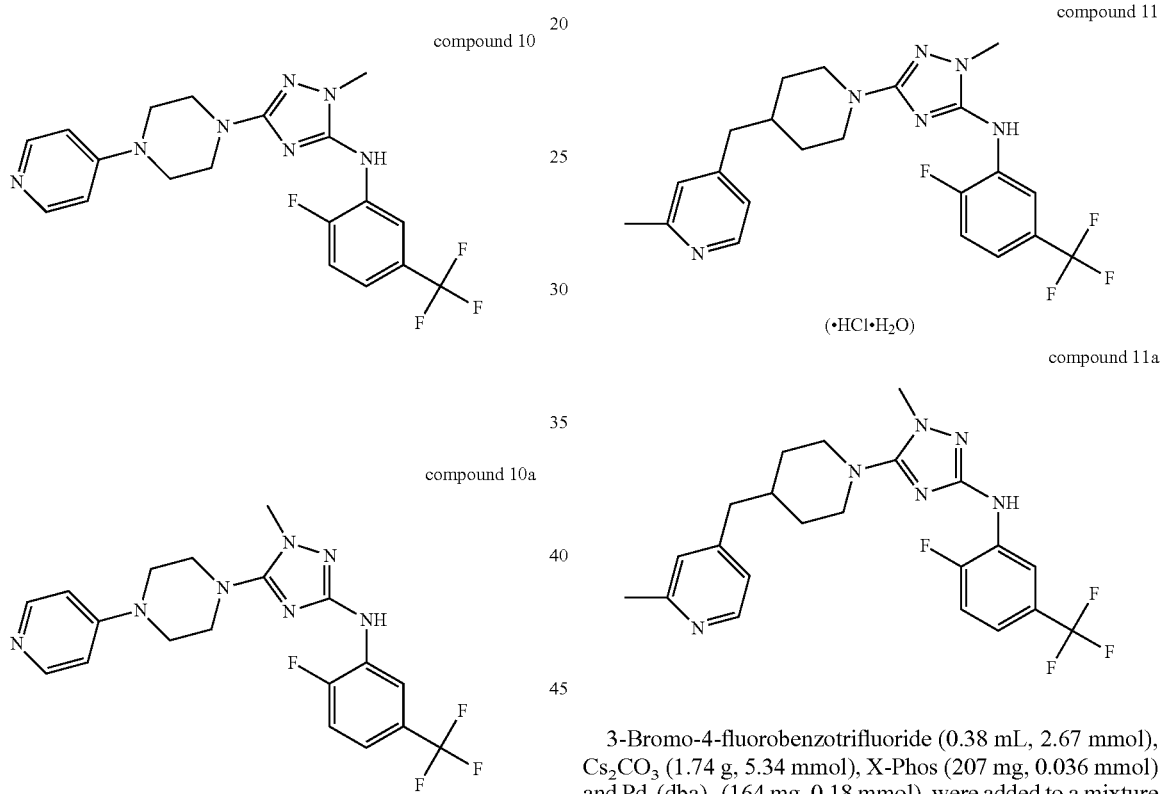

3-Bromo-4-fluorobenzotrifluoride (0.21 mL, 1.45 mmol), $Cs_2CO_3$ (943 mg, 2.89 mmol), X-Phos (92 mg, 0.19 mmol) and $Pd_2(dba)_3$ (88 mg, 0.096 mmol), were added to a mixture of intermediate 29 and intermediate 30 (250 mg, 0.96 mmol) in 2-methyl-2-propanol (20 mL) under a $N_2$ atmosphere. The r.m. was heated at 100° C. for 16 h. Then, the r.m. was cooled to r.t., water was added and the r.m. was extracted with DCM. The combined organic layers were dried ($MgSO_4$), filtered and concentrated in vacuo. The residue was purified by flash 3-Bromo-4-fluorobenzotrifluoride (0.38 mL, 2.67 mmol), $Cs_2CO_3$ (1.74 g, 5.34 mmol), X-Phos (207 mg, 0.036 mmol) and $Pd_2(dba)_3$ (164 mg, 0.18 mmol), were added to a mixture of intermediate 31 and intermediate 32 (510 mg, 1.78 mmol) in 2-methyl-2-propanol (40 mL) under a $N_2$ atmosphere. The r.m. was heated at 100° C. for 16 h. Then, the r.m. was cooled to r.t., water was added and the r.m. was extracted with DCM. The combined organic layers were dried ($MgSO_4$), filtered and concentrated in vacuo. The residue was purified by flash column chromatography (eluent: DCM/MeOH from 100/0 to 95/5). The product fractions were collected and concentrated in vacuo. Both residue was suspended in DIPE and treated with a 6 N HCl sol. in 2-propanol. Resulting precipitates were collected by filtration. The first compound impure was repurified by RP preparative HPLC [RP Vydac Denali C18-10 µm, 250 g, 5 cm); mobile phase: a gradient of (0.25% $NH_4HCO_3$ sol. in water/$CH_3CN$)]. The product fractions were collected and concentrated in vacuo. Both residue was crystallized from DIPE, filtered off and dried. Yield: 118 mg of compound 11 (13%) as HCl salt (.HCl.$H_2O$) and 97 mg of compound 11a (12%; regioisomer of compound 11).

Example B12

Preparation of Compound 12

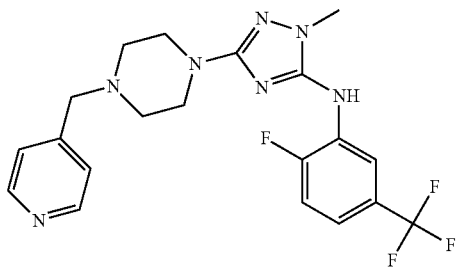 [SMILES: Cn1nc(N2CCN(Cc3ccncc3)CC2)nc1Nc1cc(C(F)(F)F)ccc1F]

3-Bromo-4-fluorobenzotrifluoride (0.20 mL, 1.37 mmol), Cs$_2$CO$_3$ (0.89 g, 2.74 mmol), X-Phos (87 mg, 0.18 mmol) and Pd$_2$(dba)$_3$ (94 mg, 0.091 mmol), were added to a sol. of intermediate 33 (250 mg, 0.91 mmol) in 2-methyl-2-propanol (20 mL) under a N$_2$ atmosphere. The r.m. was heated at 100° C. for 16 h. Then, the r.m. was cooled to r.t., water was added and the r.m. was extracted with DCM. The combined organic layers were dried (MgSO$_4$), filtered and concentrated in vacuo. The residue was purified by flash column chromatography (eluent: DCM/MeOH from 100/0 to 95/5). The product fractions were collected and concentrated in vacuo. The residue was triturated with DIPE, filtered off and dried. Yield: 210 mg of compound 12 (53%).

Example B13

Preparation of Compound 13

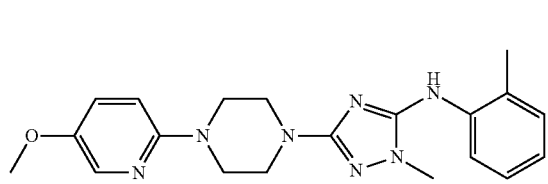 [SMILES: COc1ccc(N2CCN(c3nc(Nc4ccccc4C)n(C)n3)CC2)nc1]

1-Bromo-2-methyl-benzene (0.016 mL, 0.13 mmol), Cs$_2$CO$_3$ (0.084 g, 0.26 mmol), X-Phos (10 mg, 0.017 mmol) and Pd$_2$(dba)$_3$ (8 mg, 0.0086 mmol), were added to a sol. of intermediate 37 (25 mg, 0.086 mmol) in 2-methyl-2-propanol (2 mL) under a N$_2$ atmosphere. The r.m. was heated at 100° C. for 16 h. Then, the r.m. was cooled to r.t., water was added and the r.m. was extracted with DCM. The combined organic layers were dried (MgSO$_4$), filtered and concentrated in vacuo. The residue was purified by RP preparative HPLC [RP Vydac Denali C18-10 µm, 250 g, 5 cm); mobile phase: a gradient of (0.25% NH$_4$HCO$_3$ sol. in water/CH$_3$CN)]. The product fractions were collected and concentrated in vacuo. Yield: 7 mg of compound 13 (21%).

Example B14

Preparation of Compound 14

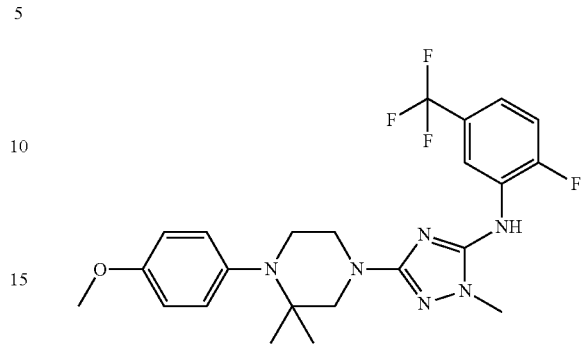

CuI (150 mg, 0.79 mmol) and N,N'-dimethylethylenediamine (0.17 mL, 1.58 mmol) were added to a mixture of 3-bromo-4-fluorobenzotrifluoride (768 mg, 3.16 mmol), intermediate 21 (250 mg, 0.79 mmol), and Cs$_2$CO$_3$ (644 mg, 1.98 mmol) in DMF (3 mL). The r.m. was heated at 170° C. for 90 min twice, the r.m. was cooled, EtOAc was added and the mixture was washed with a 1M aq. NH$_4$OH solution, water and brine. The organic layer was dried (MgSO$_4$), filtered and the solvent was evaporated in vacuo. The residue was purified by flash column chromatography (eluent: DCM/MeOH from 100/0 to 97/3). The product fractions were collected and concentrated in vacuo. Then the residue was repurified by RP preparative HPLC [RP Vydac Denali C18-10 µm, 250 g, 5 cm); mobile phase: a gradient of (0.25% NH$_4$HCO$_3$ Sol. in water)/CH$_3$CN)]. The product fractions were collected and concentrated in vacuo. Yield: 75 mg of compound 14 (20%).

Example B15

Preparation of Compound 15

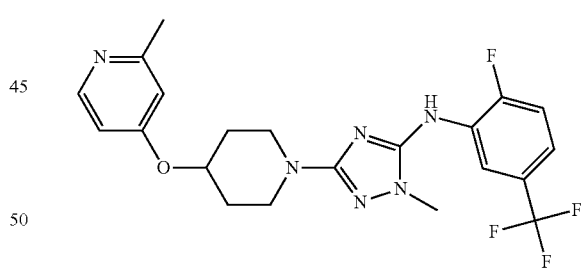

CuI (186 mg, 0.98 mmol) and N,N'-dimethylethylenediamine (0.17 mL, 1.58 mmol) were added to a mixture of 3-bromo-4-fluorobenzotrifluoride (580 mg, 3.91 mmol), intermediate 35 (282 mg, 0.98 mmol), and Cs$_2$CO$_3$ (796 mg, 2.44 mmol) in DMF (3 mL). The r.m. was heated at 170° C. for 90 min, the r.m. was cooled, EtOAc was added and the mixture was washed with a 1M aq. NH$_4$OH solution, water and brine. The organic layer was dried (MgSO$_4$), filtered and the solvent was evaporated in vacuo. The residue was purified by flash column chromatography (eluent: DCM/MeOH from 100/0 to 98/2). The product fractions were collected and concentrated in vacuo. The residue was crystallized from CH$_3$CN, filtered off and dried. Yield: 92 mg of compound 15 (21%).

Example B16

Preparation of Compound 16

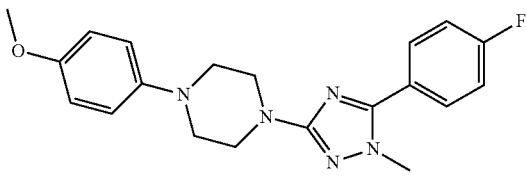 [SMILES: COc1ccc(N2CCN(c3nc(-c4ccc(F)cc4)n(C)n3)CC2)cc1]

Methylhydrazine (713 mg, 15.5 mmol) was added to a sol. of intermediate 40 (2 g, 5.16 mmol) in tert-butanol (50 mL). The r.m. was heated at reflux for 2 h. The product crystallized from the reaction mixture. The r.m. was cooled to r.t. The crystals were filtered off, washed with i-PrOH and DIPE and dried. Yield: 663 mg of compound 16 (35%).

Table 1 list the compounds that were prepared by analogy to one of the above Examples. 'Pr.' refers to the Example number according to which protocol the compound was synthesized. 'Co. No.' means compound number. 'cb' means covalent bond. Co. No. 1-3, 7-10 and 12-16 were obtained as free bases. Co. No. 4-6 and 11 were obtained as hydrochloric acid salts (determined via elemental analysis): Co. No. 4 (.HCl); Co. No. 5 (.0.8HCl); Co. No. 6 (.1.2HCl.1.5H$_2$O); Co. No. 11 (.HCl.H$_2$O).

Analytical Part
LCMS (Liquid Chromatography/Mass Spectrometry)
General Procedure A The LC measurement was performed using an Acquity UPLC (Ultra Performance Liquid Chromatography) (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds (sec) using a dwell time of 0.02 sec. The capillary needle voltage was 3.5 kV and the source temperature was maintained at 140° C. N$_2$ was used as the nebulizer gas. Data acquisition was performed with a Waters-Micromass MassLynx-Openlynx data system.

General Procedure B

The HPLC measurement was performed using an Alliance HT 2790 (Waters) system comprising a quaternary pump with degasser, an autosampler, a column oven (set at 40° C., unless otherwise indicated), a diode-array detector (DAD) and a column as specified in the respective methods below. Flow from the column was split to a MS spectrometer. The MS detector was configured with an electrospray ionization source.

Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system.

LCMS Method 1

In addition to general procedure A: Reversed phase UPLC (Ultra Performance Liquid Chromatography) was carried out on a bridged ethylsiloxane/silica hybrid (BEH) C18 column (1.7 μm, 2.1×50 mm; Waters Acquity) with a flow rate of 0.8 ml/min. Two mobile phases (25 mM ammonium acetate in H$_2$O/acetonitrile 95/5; mobile phase B: acetonitrile) were used to run a gradient condition from 95% A and 5% B to 5% A and 95% B in 1.3 minutes and hold for 0.3 minutes. An

TABLE 1

(I-a)

| Co. No. | Pr. | R$^1$ | R$^2$ | L$^1$ | R$^{4a}$ | R$^{4b}$ | X | L$^2$ | Y$^1$ | Y$^2$ | R$^5$ |
|---|---|---|---|---|---|---|---|---|---|---|---|
| 1 | B1 | 2-CH$_3$ | H | NH | CH$_3$ | CH$_3$ | N | cb | CH | COCH$_3$ | H |
| 2 | B2 | 2-CF$_3$ | H | NH | CH$_3$ | CH$_3$ | N | cb | CH | COCH$_3$ | H |
| 3 | B3 | 2-CF$_3$ | 3-F | NH | CH$_3$ | CH$_3$ | N | cb | CH | COCH$_3$ | H |
| 4 | B4 | 3-OCF$_3$ | H | NH | CH$_3$ | CH$_3$ | N | cb | CH | COCH$_3$ | H |
| 5 | B5 | 3-F | 5-CF$_3$ | NH | CH$_3$ | CH$_3$ | N | cb | CH | COCH$_3$ | H |
| 6 | B6 | 2-CH$_3$ | 4-F | NH | CH$_3$ | CH$_3$ | N | cb | CH | COCH$_3$ | H |
| 7 | B7 | 2-F | 5-CF$_3$ | NH | H | H | CH | O | CH | N | H |
| 8 | B8 | 2-F | 5-CF$_3$ | NH | H | H | CH | O | N | N | CH$_3$ |
| 9 | B9 | 2-F | 5-CF$_3$ | NH | H | H | N | cb | CH | COCH$_3$ | H |
| 10 | B10 | 2-F | 5-CF$_3$ | NH | H | H | N | cb | CH | N | H |
| 11 | B11 | 2-F | 5-CF$_3$ | NH | H | H | CH | CH$_2$ | CH | N | CH$_3$ |
| 12 | B12 | 2-F | 5-CF$_3$ | NH | H | H | N | CH$_2$ | CH | N | H |
| 13 | B13 | 2-CH$_3$ | H | NH | H | H | N | cb | N | COCH$_3$ | H |
| 14 | B14 | 2-F | 5-CF$_3$ | NH | CH$_3$ | CH$_3$ | N | cb | CH | COCH$_3$ | H |
| 15 | B15 | 2-F | 5-CF$_3$ | NH | H | H | CH | O | CH | N | CH$_3$ |
| 16 | B16 | 4-F | H | cb | H | H | N | cb | CH | COCH$_3$ | H | injection volume of 0.5 μl was used. Cone voltage was 30 V for positive ionization mode and 30 V for negative ionization mode.

LCMS Method 2

In addition to general procedure A: Reversed phase UPLC was carried out on a bridged ethylsiloxane/silica hybrid (BEH) C18 column (1.7 μm, 2.1×50 mm; Waters Acquity) with a flow rate of 0.8 ml/min. Two mobile phases (mobile phase A: 0.1% formic acid in $H_2O$/methanol 95/5; mobile phase B: methanol) were used to run a gradient condition from 95% A and 5% B to 5% A and 95% B in 1.3 minutes and hold for 0.2 minutes.

An injection volume of 0.5 μl was used. Cone voltage was 10 V for positive ionization mode and 20 V for negative ionization mode.

LCMS Method 3

In addition to general procedure B: Reversed phase HPLC was carried out on an Xterra MS C18 column (3.5 μm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 1% A, 49% B and 50% C in 6.5 minutes, to 1% A and 99% B in 1 minute and hold these conditions for 1 minute and reequilibrate with 100% A for 1.5 minutes. An injection volume of 101 was used. Cone voltage was 10 V for positive ionization mode and 20 V for negative ionization mode.

LCMS Method 4

In addition to general procedure A: Reversed phase UPLC was carried out on a bridged ethylsiloxane/silica hybrid (BEH) C18 column (1.7 μm, 2.1×50 mm; Waters Acquity) with a flow rate of 0.8 ml/min. Two mobile phases (mobile phase A: 10 mM ammonium acetate in $H_2O$/acetonitrile 95/5; mobile phase B: acetonitrile) were used to run a gradient condition from 95% A and 5% B to 5% A and 95% B in 1.3 minutes and hold for 0.2 minutes. An injection volume of 0.5 μl was used. Cone voltage was 10 V for positive ionization mode and 20 V for negative ionization mode.

Melting Points

For some compounds melting points (m.p.) were determined with a DSC823e (Mettler-Toledo). Melting points were measured with a temperature gradient of 30° C./min. Maximum temperature was 400° C. Values are peak values.

The results of the analytical measurements are shown in table 2a.

TABLE 2a

Retention time ($R_t$) in min., $[M + H]^+$ peak (protonated molecule), LCMS method and m.p. (melting point in ° C.). (n.d. means not determined)

| Co. No. | $R_t$ | $[M + H]^+$ | LCMS Method | m.p. (° C.) |
|---|---|---|---|---|
| 1 | 1.15 | 407 | 1 | 156.8 |
| 2 | 1.24 | 461 | 1 | n.d. |
| 3 | 1.23 | 479 | 1 | n.d. |
| 4 | 1.29 | 477 | 1 | n.d. |
| 5 | 1.33 | 479 | 1 | n.d. |
| 6 | 1.15 | 425 | 1 | n.d. |
| 7 | 1.02 | 437 | 1 | n.d. |
| 8 | 1.08 | 452 | 1 | 158.0 |
| 9 | 1.18 | 451 | 1 | 145.4 |
| 10 | 0.86 | 422 | 1 | 261.8 |
| 11 | 1.13 | 449 | 1 | n.d. |
| 12 | 0.97 | 436 | 1 | 161.4 |
| 13 | 0.98 | 380 | 4 | n.d. |
| 14 | 1.28 | 479 | 1 | n.d. |
| 15 | 5.95 | 451 | 3 | 177.4 |
| 16 | 1.29 | 368 | 2 | 191.6 |

NMR

For a number of compounds, $^1H$ NMR spectra were recorded on a Bruker DPX-360 or on a Bruker DPX-400 spectrometer with standard pulse sequences, operating at 360 MHz and 400 MHz respectively, using CHLOROFORM-d (deuterated chloroform, $CDCl_3$) or DMSO-$d_6$ (deuterated DMSO, dimethyl-$d_6$ sulfoxide) as solvents. Chemical shifts (6) are reported in parts per million (ppm) relative to tetramethylsilane (TMS), which was used as internal standard.

TABLE 2b $^1H$ NMR results

| Co. No. | $^1H$ NMR result |
|---|---|
| 1 | (360 MHz, DMSO-$d_6$) δ ppm 0.96 (s, 6 H), 2.23 (s, 3 H), 3.00-3.06 (m, 2 H), 3.08 (s, 2 H), 3.21-3.31 (m, 2 H), 3.51 (s, 3 H), 3.72 (s, 3 H), 6.83 (m, J = 8.6 Hz, 2 H), 6.92 (t, J = 7.3 Hz, 1 H), 7.06 (m, J = 8.7 Hz, 2 H), 7.12 (t, J = 7.5 Hz, 1 H), 7.16 (d, J = 7.4 Hz, 1 H), 7.27 (d, J = 8.0 Hz, 1 H), 7.79 (s, 1 H) |
| 6 | (400 MHz, DMSO-$d_6$, 125° C.) δ ppm 1.14 (s, 6 H), 2.24 (s, 3 H), 3.38 (br. s., 2 H), 3.42 (br. s., 2 H), 3.50 (s, 3 H), 3.58 (br. s., 2 H), 3.77 (s, 3 H), 6.83-6.99 (m, 4 H), 7.29 (dd, J = 8.9, 5.7 Hz, 1 H), 7.40 (br. s., 2 H) |
| 8 | (360 MHz, DMSO-$d_6$) δ ppm 1.61-1.76 (m, 2 H), 2.02 (d, J = 12.7 Hz, 2 H), 2.36 (s, 3 H), 3.11 (ddd, J = 12.6, 9.7, 2.6 Hz, 2 H), 3.60 (s, 3 H), 3.67 (dt, J = 12.8, 4.2 Hz, 2 H), 5.24 (tt, J = 8.6, 4.2 Hz, 1 H), 6.79 (s, 1 H), 7.27-7.36 (m, 1 H), 7.47 (dd, J = 11.1, 8.5 Hz, 1 H), 8.25 (dd, J = 7 .7 , 2.4 Hz, 1 H), 8.64 (s, 1 H), 8.90 (s, 1 H) |
| 14 | (360 MHz, CHLOROFORM-d) δ ppm 1.08 (s, 6 H), 3.16-3.24 (m, 2 H), 3.30 (s, 2 H), 3.50-3.57 (m, 2 H), 3.64 (s, 3 H), 3.80 (s, 3 H), 6.22 (br. s., 1 H), 6.82 (d, J = 8.6 Hz, 2 H), 7.09 (d, J = 8.6 Hz, 2 H), 7.13-7.24 (m, 2 H), 8.41 (d, J = 7.7 Hz, 1 H) |
| 16 | (400 MHz, DMSO-d6) δ ppm 3.02-3.15 (m, 4 H), 3.40-3.49 (m, 4 H), 3.69 (s, 3 H), 3.79 (s, 3 H), 6.84 (d, J = 9.1 Hz, 2 H), 6.95 (d, J = 9.2 Hz, 2 H), 7.37 (t, J = 8.9 Hz, 2 H), 7.78 (dd, J = 8.8, 5.4 Hz, 2 H) |

Pharmacology
A) Screening of the Compounds of the Invention for γ-Secretase-Modulating Activity Screening was carried out using SKNBE2 cells carrying the APP 695-wild type, grown in Dulbecco's Modified Eagle's Medium/Nutrient mixture F-12 (DMEM/NUT-mix F-12) (HAM) provided by Invitrogen (cat no. 10371-029) containing 5% Serum/Fe supplemented with 1% non-essential amino acids, 1-glutamine 2 mM, Hepes 15 mM, penicillin 50 U/ml (units/ml) en streptomycin 50 g/ml. Cells were grown to near confluency.

The screening was performed using a modification of the assay as described in Citron et al (1997) Nature Medicine 3: 67. Briefly, cells were plated in a 384-well plate at $10^4$ cells/well in Ultraculture (Lonza, BE12-725F) supplemented with 1% glutamine (Invitrogen, 25030-024), 1% non-essential amino acid (NEAA), penicillin 50 U/ml en streptomycin 50 g/ml in the presence of test compound at different test concentrations. The cell/compound mixture was incubated overnight at 37° C., 5% $CO_2$. The next day the media were assayed by two sandwich immuno-assays, for Aβ42 and Aβtotal.

Aβtotal and Aβ42 concentrations were quantified in the cell supernatant using the Aphalisa technology (Perkin Elmer). Alphalisa is a sandwich assay using biotinylated antibody attached to streptavidin coated donorbeads and antibody conjugated to acceptor beads. In the presence of antigen, the beads come into close proximity. The excitation of the donor beads provokes the release of singlet oxygen molecules that trigger a cascade of energy transfer in the acceptor beads, resulting in light emission.

To quantify the amount of Aβ42 in the cell supernatant, monoclonal antibody specific to the C-terminus of Aβ42 (JRF/cAB42/26) was coupled to the receptor beads and biotinylated antibody specific to the N-terminus of Aβ (JRF/ABN/25) was used to react with the donor beads. T quantify the amount of Aβtotal in the cell supernatant, monoclonal antibody specifc to the N-terminus of Aβ (JRF/AβN/25) was coupled to the receptor beads and biotinylated antibody specific to the mid region of Aβ (biotinylated 4G8) was used to react with the donor beads.

To obtain the values reported in Table 3, the data are calculated as percentage of the maximum amount of amyloid Beta 42 measured in the absence of the test compound. The sigmoidal dose response curves were analyzed using non-linear regression analysis with percentage of the control plotted against the log concentration of the compound. A 4-parameter equation was used to determine the $IC_{50}$.

TABLE 3

| Co. No. | IC50 Aβ42 (μM) | IC50 Aβtotal (μM) |
| --- | --- | --- |
| 1 | 0.05 | >10 |
| 2 | 0.09 | >10 |
| 3 | 0.05 | >10 |
| 4 | 0.07 | >10 |
| 5 | 0.14 | >10 |
| 6 | 0.05 | >10 |
| 7 | 0.72 | >10 |
| 8 | 0.95 | >10 |
| 9 | 0.56 | >10 |
| 10 | 4.90 | >10 |
| 11 | 6.92 | >10 |
| 12 | >10 | >10 |
| 13 | n.d. | n.d. |
| 14 | 0.11 | >10 |
| 15 | 0.25 | >10 |
| 16 | 4.07 | >10 |

B) Demonstration of In Vivo Efficacy

Aβ42 lowering agents of the invention can be used to treat AD in mammals such as humans or alternatively demonstrating efficacy in animal models such as, but not limited to, the mouse, rat, or guinea pig. The mammal may not be diagnosed with AD, or may not have a genetic predisposition for AD, but may be transgenic such that it overproduces and eventually deposits Aβ in a manner similar to that seen in humans afflicted with AD.

Aβ42 lowering agents can be administered in any standard form using any standard method. For example, but not limited to, Aβ42 lowering agents can be in the form of liquid, tablets or capsules that are taken orally or by injection. Aβ42 lowering agents can be administered at any dose that is sufficient to significantly reduce levels of Aβ42 in the blood, blood plasma, serum, cerebrospinal fluid (CSF), or brain.

To determine whether acute administration of an Aβ42 lowering agent would reduce Aβ42 levels in vivo, non-transgenic rodents, e.g. mice or rats were used. Animals treated with the Aβ42 lowering agent were examined and compared to those untreated or treated with vehicle and brain levels of soluble Aβ42 and total Aβ were quantitated by standard techniques, for example, using ELISA. Treatment periods varied from hours (h) to days and were adjusted based on the results of the Aβ42 lowering once a time course of onset of effect could be established.

A typical protocol for measuring Aβ42 lowering in vivo is shown but it is only one of many variations that could be used to optimize the levels of detectable A3. For example, Aβ42 lowering compounds were formulated in 20% of Captisol® (a sulfobutyl ether of β-cyclodextrin) in water or 20% hydroxypropyl 0 cyclodextrin. The Aβ42 lowering agents were administered as a single oral dose or by any acceptable route of administration to overnight fasted animals. After 4 h, the animals were sacrificed and Aβ42 levels were analysed.

Blood was collected by decapitation and exsanguinations in EDTA-treated collection tubes. Blood was centrifuged at 1900 g for 10 minutes (min) at 4° C. and the plasma recovered and flash frozen for later analysis. The brain was removed from the cranium and hindbrain. The cerebellum was removed and the left and right hemisphere were separated. The left hemisphere was stored at −18° C. for quantitative analysis of test compound levels. The right hemisphere was rinsed with phosphate-buffered saline (PBS) buffer and immediately frozen on dry ice and stored at −80° C. until homogenization for biochemical assays.

Mouse brains from non-transgenic animals were resuspended in 8 volumes of 0.4% DEA (diethylamine)/50 mM NaCl containing protease inhibitors (Roche-11873580001 or 04693159001) per gram of tissue, e.g. for 0.158 g brain, add 1.264 ml of 0.4% DEA. All samples were homogenized in the FastPrep-24 system (MP Biomedicals) using lysing matrix D (MPBio #6913-100) at 6 m/s for 20 seconds. Homogenates were centrifuged at 221.300×g for 50 min. The resulting high speed supernatants were then transferred to fresh eppendorf tubes. Nine parts of supernatant were neutralized with 1 part 0.5 M Tris-HCl pH 6.8 and used to quantify Aβtotal and Aβ42.

To quantify the amount of Aβtotal and Aβ42 in the soluble fraction of the brain homogenates, Enzyme-Linked-Immunosorbent-Assays were used. Briefly, the standards (a dilution of synthetic Aβ1-40 and Aβ1-42, Bachem) were prepared in 1.5 ml Eppendorf tube in Ultraculture, with final concentrations ranging from 10000 to 0.3 pg/ml. The samples and standards were co-incubated with HRPO-labelled N-terminal antibody for Aβ42 detection and with the biotinylated middomain antibody 4G8 for Aβtotal detection. 50 μl of conjugate/sample or conjugate/standards mixtures were then added to the antibody-coated plate (the capture antibodies selectively recognize the C-terminal end of Aβ42, antibody JRF/cAβ42/26, for Aβ42 detection and the N-terminus of Aβ, antibody JRF/rAβ/2, for Aβtotal detection). The plate was allowed to incubate overnight at 4° C. in order to allow formation of the antibody-amyloid complex. Following this incubation and subsequent wash steps the ELISA for Aβ42 quantification was finished by addition of Quanta Blu fluorogenic peroxidase substrate according to the manufacturer's instructions (Pierce Corp., Rockford, Il). A reading was performed after 10 to 15 min (excitation 320 nm/emission 420 nm).

For Aβtotal detection, a Streptavidine-Peroxidase-Conjugate was added, followed 60 min later by an additional wash step and addition of Quanta Blu fluorogenic peroxidase substrate according to the manufacturer's instructions (Pierce Corp., Rockford, Il). A reading was performed after 10 to 15 min (excitation 320 nm/emission 420 nm).

In this model at least 20% Aβ42 lowering compared to untreated animals would be advantageous.

The results are shown in Table 4 (dose 30 mg/kg oral dosing) (value for untreated animals as control (Ctrl) was set at 100):

| Co. No. | Aβ42 (% vs Ctrl)_Mean | Aβtotal (% vs Ctrl)_Mean |
|---|---|---|
| 14 | 78 | 111 |
| 6 | 45 | 109 |
| 1 | 50 | 107 |

Composition Examples

"Active ingredient" (a.i.) as used throughout these examples relates to a compound of Formula (I), including any stereochemically isomeric form thereof, a pharmaceutically acceptable salt thereof or a solvate thereof; in particular to any one of the exemplified compounds.

Typical examples of recipes for the formulation of the invention are as follows:

1. Tablets

| Active ingredient | 5 to 50 mg |
|---|---|
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

4. Ointment

| Active ingredient | 5 to 1000 mg |
|---|---|
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

The invention claimed is:

1. A compound of Formula (I)

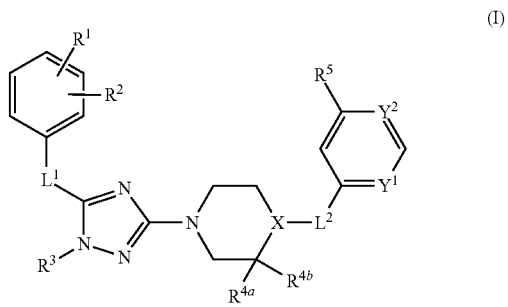

or a stereoisomeric form thereof, wherein
$R^1$ and $R^2$ independently are selected from the group consisting of hydrogen, halo, $C_{1-4}$ alkyl, $C_{1-4}$ alkyloxy, $C_{1-4}$ alkyl substituted with one or more halo substituents, and $C_{1-4}$ alkyloxy substituted with one or more halo substituents;
$L^1$ is $NR^6$, O, carbonyl or a covalent bond; wherein $R^6$ is hydrogen or $C_{1-4}$ alkyl;
$R^3$ represents $C_{1-4}$ alkyl;
$R^{4a}$ and $R^{4b}$ independently are selected from the group consisting of hydrogen and $C_{1-4}$ alkyl;
X is N or CH;
$L^2$ is O, $CH_2$ or a covalent bond; provided that when $L^2$ is O, then X is CH;
$R^5$ is hydrogen or $C_{1-4}$ alkyl;
$Y^1$ is CH or N;
$Y^2$ is $CR^7$ or N; wherein $R^7$ represents H or $C_{1-4}$ alkyloxy;
or a pharmaceutically acceptable addition salt or a hydrate thereof.

2. The compound according to claim 1 wherein $R^{4a}$ and $R^{4b}$ are the same and both represent hydrogen or $C_{1-4}$ alkyl.

3. The compound according to claim 1, wherein
$R^1$ and $R^2$ independently are selected from the group consisting of hydrogen, halo, $C_{1-4}$ alkyl, $C_{1-4}$ alkyl substituted with one or more halo substituents, and $C_{1-4}$ alkyloxy substituted with one or more halo substituents;
$L^1$ is NH or a covalent bond;
$R^3$ represents $C_{1-4}$ alkyl;
$R^{4a}$ and $R^{4b}$ are the same and both represent hydrogen or $C_{1-4}$ alkyl;
X is N or CH;
$L^2$ is O, $CH_2$ or a covalent bond provided that when $L^2$ is O, then X is CH;
$R^5$ is hydrogen or $C_{1-4}$ alkyl;
$Y^1$ is CH or N; and
$Y^2$ is $CR^7$ or N; wherein $R^7$ represents $C_{1-4}$ alkyloxy.

4. The compound according to claim 1, wherein
$R^1$ and $R^2$ independently are selected from the group consisting of hydrogen, fluoro, methyl, trifluoromethyl, and trifluoromethoxy;
$L^1$ is NH or a covalent bond;
$R^3$ represents methyl;
$R^{4a}$ and $R^{4b}$ are the same and both represent hydrogen or methyl;
X is N or CH;
$L^2$ is O, $CH_2$ or a covalent bond; provided that when $L^2$ is O, then X is CH;
$R^5$ is hydrogen or methyl;
$Y^1$ is CH or N;
$Y^2$ is $CR^7$ or N; wherein $R^7$ represents methoxy.

5. The compound according to claim 1, wherein
$R^1$ is in the 2-position and is selected from the group consisting of halo, $C_{1-4}$alkyl, $C_{1-4}$alkyloxy, $C_{1-4}$alkyl substituted with one or more halo substituents, and $C_1$ alkyloxy substituted with one or more halo substituents; and
wherein $R^2$ is selected from the group consisting of hydrogen, halo, $C_{1-4}$alkyl, $C_{1-4}$ alkyloxy, $C_{1-4}$alkyl substituted with one or more halo substituents, and $C_{1-4}$ alkyloxy substituted with one or more halo substituents.

6. The compound according to claim 1, wherein
$R^1$ represents methyl and is in the 2-position, and $R^2$ represents hydrogen or fluoro and is in the 4-position;
$L^1$ is NH;
$R^3$ represents methyl;
$R^{4a}$ and $R^{4b}$ are the same and both represent methyl;
X is N;
$L^2$ is a covalent bond;
$R^5$ is hydrogen;
$Y^1$ is CH;
$Y^2$ is $CR^7$; wherein $R^7$ represents methoxy.

7. The compound according to claim 1, wherein $L^1$ is $NR^6$ or a covalent bond.

8. The compound according to claim 7 wherein $L^1$ is NH.

9. The compound according to claim 1 wherein X is N and $L^2$ is a covalent bond.

10. The compound according to claim 1 wherein the compound is selected from the group consisting of
3-[4-(4-methoxyphenyl)-3,3-dimethyl-1-piperazinyl]-1-methyl-N-(2-methylphenyl)-1H-1,2,4-triazol-5-amine,
N-(4-fluoro-2-methylphenyl)-3-[4-(4-methoxyphenyl)-3,3-dimethyl-1-piperazinyl]-1-methyl-1H-1,2,4-triazol-5-amine, and
N-(4-fluoro-2-methylphenyl)-3-[4-(4-methoxyphenyl)-3,3-dimethyl-1-piperazinyl]-1-methyl-1H-1,2,4-triazol-5-amine.1.2 HCl.1.5 $H_2O$,
stereoisomeric forms thereof, and pharmaceutically acceptable addition salts and hydrates thereof.

11. A pharmaceutical composition comprising a pharmaceutically acceptable carrier and, as active ingredient, a therapeutically effective amount of a compound as defined in any one of claims 1 to 10.

12. A method for the treatment of Alzheimer's disease comprising administering to a subject in need thereof a compound as defined in any one of claims 1 to 10.

* * * * *